(12) United States Patent
Minamizato et al.

(10) Patent No.: US 9,521,944 B2
(45) Date of Patent: Dec. 20, 2016

(54) ENDOSCOPE SYSTEM FOR DISPLAYING AN ORGAN MODEL IMAGE TO WHICH AN ENDOSCOPE IMAGE IS PASTED

(71) Applicant: OLYMPUS CORPORATION, Toyko (JP)

(72) Inventors: Miho Minamizato, Tachikawa (JP); Jun Hasegawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/794,111

(22) Filed: Jul. 8, 2015

(65) Prior Publication Data

US 2015/0305600 A1    Oct. 29, 2015

Related U.S. Application Data

(63) Continuation of application No. PCT/JP2014/053942, filed on Feb. 19, 2014.

(30) Foreign Application Priority Data

Mar. 19, 2013   (JP) ................................ 2013-056907

(51) Int. Cl.
*A61B 1/04*     (2006.01)
*A61B 1/045*    (2006.01)
(Continued)

(52) U.S. Cl.
CPC ........... *A61B 1/00096* (2013.01); *A61B 1/005* (2013.01); *A61B 1/0005* (2013.01);
(Continued)

(58) Field of Classification Search
CPC ... A61B 1/00009; A61B 1/0005; A61B 1/307; A61B 1/00181; A61B 1/00183; A61B 5/7425; G06T 11/60; G06T 2207/10068; G06T 7/0046
See application file for complete search history.

(56) References Cited

U.S. PATENT DOCUMENTS

2004/0249247 A1* 12/2004 Iddan ................... A61B 1/0005
                                                              600/170
2007/0060792 A1*  3/2007 Draxinger .......... A61B 1/00009
                                                              600/117
(Continued)

FOREIGN PATENT DOCUMENTS

EP       2305094 A1     4/2011
JP    2008-220672 A     9/2008
(Continued)

OTHER PUBLICATIONS

International Search Report dated May 27, 2014 issued in PCT/JP2014/053942.
(Continued)

*Primary Examiner* — John P Leubecker
(74) *Attorney, Agent, or Firm* — Scully, Scott, Murphy & Presser, P.C.

(57) ABSTRACT

An endoscope system includes a determining section that determines whether or not an image pickup device is moving at a predetermined speed or higher based on position/direction information and determines, when the image pickup device is not moving at the predetermined speed or higher, that a subject internal image is an image that can be pasted onto a model image of a predetermined organ in a state where the position/direction information of an objective optical window and position/direction information in a coordinate system of the predetermined organ model image are associated with each other, and an image pasting section that reads the subject internal image determined to be the image that can be pasted from the memory and pastes the (Continued)

subject internal image onto the model image of the predetermined organ based on the position/direction information.

5 Claims, 18 Drawing Sheets

(51) Int. Cl.
*A61B 1/00* (2006.01)
*A61B 1/307* (2006.01)
*A61B 1/005* (2006.01)
*G06T 7/00* (2006.01)
*H04N 1/00* (2006.01)

(52) U.S. Cl.
CPC ........ *A61B 1/00009* (2013.01); *A61B 1/0051* (2013.01); *A61B 1/00064* (2013.01); *A61B 1/00193* (2013.01); *A61B 1/307* (2013.01); *G06T 7/00* (2013.01); *H04N 1/00183* (2013.01); *A61B 1/04* (2013.01); *A61B 2034/2051* (2016.02); *G06T 2207/10068* (2013.01); *G06T 2207/30004* (2013.01); *G06T 2207/30168* (2013.01)

(56) References Cited

U.S. PATENT DOCUMENTS

| | | | |
|---|---|---|---|
| 2007/0149846 A1* | 6/2007 | Chen | A61B 1/00009 600/117 |
| 2007/0161853 A1 | 7/2007 | Yagi et al. | |
| 2007/0161854 A1 | 7/2007 | Alamaro et al. | |
| 2009/0259102 A1* | 10/2009 | Koninckx | A61B 1/00181 600/111 |
| 2011/0077462 A1 | 3/2011 | Saitou et al. | |
| 2011/0242301 A1* | 10/2011 | Morita | A61B 1/00009 348/65 |
| 2012/0154562 A1* | 6/2012 | Munzenmayer | G06K 9/32 348/65 |
| 2012/0289825 A1* | 11/2012 | Rai | A61B 6/463 600/425 |
| 2014/0296644 A1* | 10/2014 | Zilberstein | A61B 1/06 600/178 |
| 2015/0216403 A1* | 8/2015 | Whitmore, III | A61B 1/307 600/103 |
| 2015/0221116 A1* | 8/2015 | Wu | A61B 1/00009 382/128 |

FOREIGN PATENT DOCUMENTS

| | | |
|---|---|---|
| JP | 2010-240000 A | 10/2010 |
| JP | 2011-050470 A | 3/2011 |
| JP | 2011-092690 A | 5/2011 |
| WO | WO 2005/077253 A1 | 8/2005 |

OTHER PUBLICATIONS

Japanese Office Action dated Jan. 13, 2015 issued in JP 2014-533501.

Extended Supplementary European Search Report dated Aug. 18, 2016 in related European Application No. 14 76 7681.1.

* cited by examiner

ENDOSCOPE SYSTEM FOR DISPLAYING AN ORGAN MODEL IMAGE TO WHICH AN ENDOSCOPE IMAGE IS PASTED

CROSS REFERENCE TO RELATED APPLICATION

This application is a continuation application of PCT/JP2014/053942 filed on Feb. 19, 2014 and claims benefit of Japanese Application No. 2013-056907 filed in Japan on Mar. 19, 2013, the entire contents of which are incorporated herein by this reference.

BACKGROUND OF THE INVENTION

1. Field of the Invention

The present invention relates to an endoscope system, and more particularly, to an endoscope system for displaying an organ model image to which an endoscope image is pasted.

2. Description of the Related Art

Conventionally, endoscope systems have been widely used in medical and industrial fields. In endoscope systems in the medical field, for example, an operator inserts an insertion portion of an endoscope into a subject and an endoscope image obtained through an observation window provided at a distal end portion of the insertion portion is displayed on a display apparatus. The operator can perform an endoscope inspection by observing the displayed endoscope image. The endoscope system can also record endoscope images. For example, medical doctors can use an endoscope image of a recorded lesioned part as part of a clinical record.

In recent years, capsule-type endoscope systems are also commercialized and when a patient swallows the capsule-type endoscope, the capsule-type endoscope picks up images of the inside of the body and records the images while moving through the body.

In the case of a capsule endoscope, since a huge number of images are acquired, various techniques are being proposed such as a technique of extracting only images of a region to be observed such as a lesioned part from among many acquired images and a technique as disclosed in Japanese Patent Application Laid-Open Publication No. 2010-240000 of generating diagnostic images using images with high priority based on characteristic parameters when a plurality of images are pasted onto a 3D model.

Japanese Patent Application Laid-Open Publication No. 2008-220672 also proposes an endoscope apparatus that stores endoscope images according to an insertion length of the insertion portion.

An endoscope inspection may be performed over again to observe a state of a lesioned part discovered in a previous endoscope inspection or a treatment may be performed on a lesioned part discovered in a previous endoscope inspection using an endoscope.

For that purpose, a medical doctor fills in a clinical record with a position of the lesioned part discovered in inspection in the organ to be examined. For example, when the organ to be inspected is a bladder, the position of the lesioned part is specified by marking a developed view (schema) of the bladder written in the clinical record.

SUMMARY OF THE INVENTION

An endoscope system according to an aspect of the present invention is provided with an insertion portion that is inserted into a subject; an objective optical window provided on a distal end side of the insertion portion to receive light from the subject; an image pickup section that picks up an image of an interior of the subject using the light incident on the objective optical window; a position information acquiring section that acquires position information of the objective optical window; a storage section that stores a predetermined organ model image in the subject; a recording section that records, in the storage section, a subject internal image acquired by the image pickup section and position/direction information acquired by the position information acquiring section in association with each other; a determining section that determines whether or not the image pickup section is moving at a predetermined speed or higher based on the position/direction information and determines, when the image pickup section is not moving at the predetermined speed or higher, that the subject internal image is an image that can be pasted onto a model image of the predetermined organ in a state where the position/direction information of the objective optical window and the position/direction information in a coordinate system of the predetermined organ model image are associated with each other; and an image pasting section that reads the subject internal image determined by the determining section to be the image that can be pasted from the storage section and pastes the subject internal image onto the model image of the predetermined organ based on the position/direction information.

DETAILED DESCRIPTION OF THE PREFERRED EMBODIMENT

Hereinafter, an embodiment of the present invention will be described with reference to the accompanying drawings.

The embodiment of the present invention will be described hereinafter using a case where an endoscope image of an interior of the bladder is acquired as an example.

(Configuration)

Figure 1:
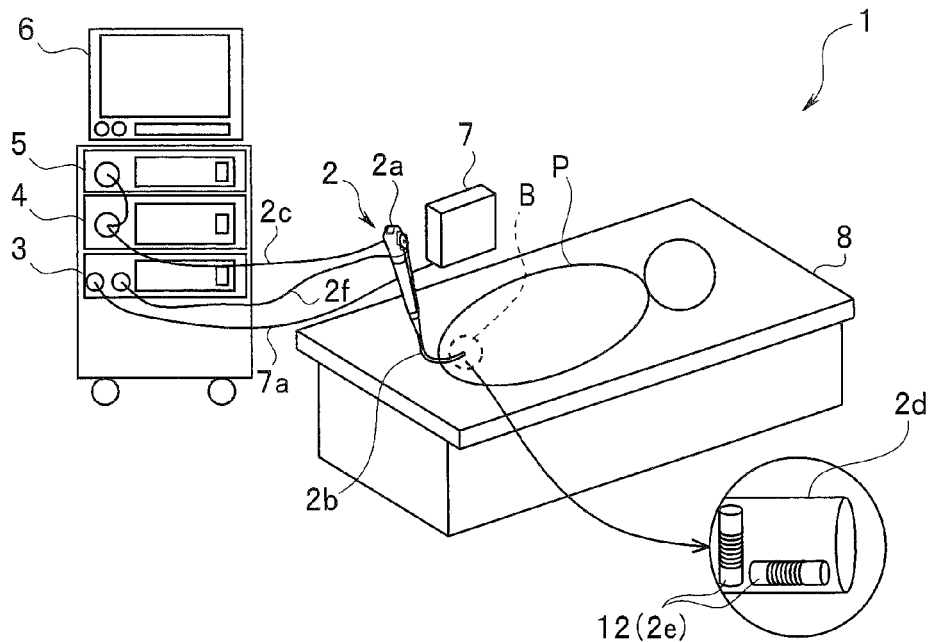
FIG. 1 is a configuration diagram illustrating a configuration of an endoscope system according to an embodiment of the present invention.
Figure 2:
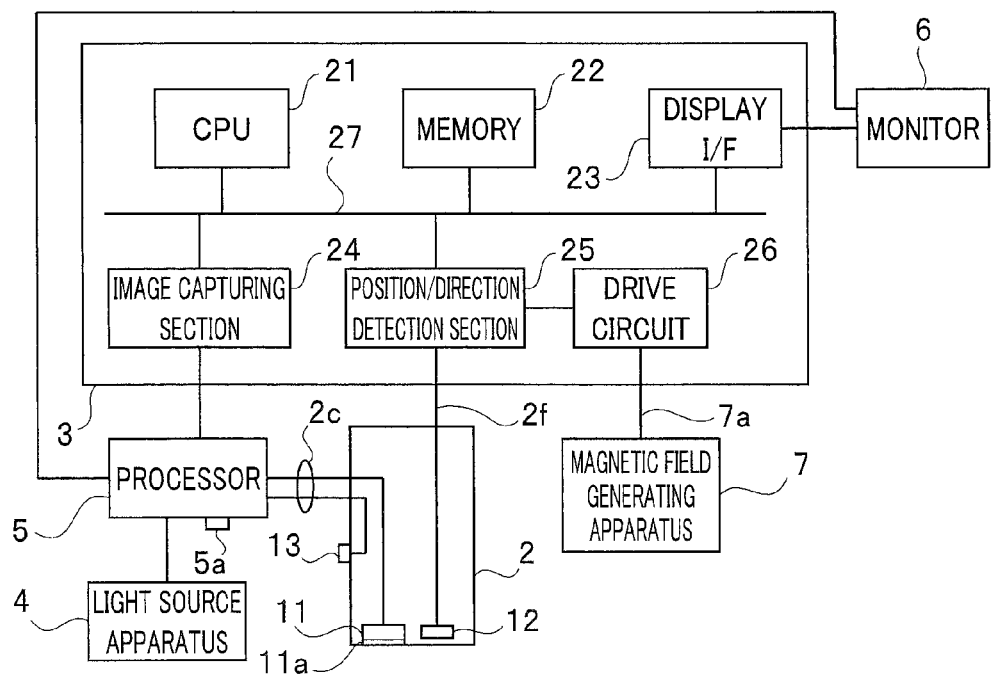
FIG. 2 is a block diagram illustrating a configuration of an endoscope system 1 according to the embodiment of the present invention.

FIG. 1 is a configuration diagram illustrating a configuration of an endoscope system according to the present embodiment. FIG. 2 is a block diagram illustrating a configuration of an endoscope system 1. The endoscope system 1 is constructed of an endoscope 2, a recording apparatus 3, a light source apparatus 4, a processor 5, a monitor 6, and a magnetic field generating apparatus 7. The endoscope system 1 has two observation modes; normal light observation and special light observation. A medical doctor who is an inspector performs an endoscope inspection of a bladder B of a patient P lying on his/her back on a bed 8.

The endoscope 2 includes an operation portion 2a, a flexible insertion portion 2b which is inserted into a subject and a universal cable 2c. The endoscope 2 is an endoscope for a bladder inspection.

Though not shown, a light guide is inserted into the universal cable 2c and the endoscope 2 is configured such that illuminating light from the light source apparatus 4 is passed through the light guide and emitted from a distal end portion 2d of an insertion portion 2b.

Furthermore, as shown in FIG. 2, an image pickup device 11 is provided at the distal end portion 2d of the insertion portion 2b and an image of a region in the bladder B illuminated with illuminating light of the light source apparatus 4 is picked up by the image pickup device 11 via an objective optical window 11a. The objective optical window 11a is provided on the distal end side of the insertion portion 2 and receives light from the subject. That is, the image pickup device 11 constitutes an image pickup section that is inserted into the subject and picks up an image of the interior of the subject using light incident from the objective optical window 11a. An image pickup signal acquired by the image pickup device 11 is supplied to the processor 5 via a signal line in the universal cable 2c and the image pickup signal is subjected to image processing in the processor 5.

The processor 5 includes a change-over switch 5a for switching between observation modes and the processor 5 generates an endoscope image corresponding to the observation mode specified by the change-over switch 5a.

The generated endoscope image is outputted from the processor 5 to the monitor 6 and the live endoscope image is displayed on the monitor 6. A medical doctor who performs an inspection (hereinafter referred to as "inspector") inserts the distal end portion 2d of the insertion portion 2b from the urethra of the patient P and can thereby observe the interior of the bladder B of the patient P (shown by a dotted line in FIG. 1).

Furthermore, a magnetic sensor 12 is disposed at the distal end portion 2d of the insertion portion 2b. More specifically, the magnetic sensor 12 including two coils 2e is provided in the vicinity of the objective optical window 11a of the distal end portion 2d. Therefore, the magnetic sensor 12 is a 6-axis sensor. A signal line 2f of the magnetic sensor 12 extends from the endoscope 2 and is connected to the recording apparatus 3.

The magnetic field generating apparatus 7 generates a predetermined magnetic field and the magnetic sensor 12 detects a magnetic field generated by the magnetic field generating apparatus 7. The detection signal of the magnetic field is supplied from the endoscope 2 to the recording apparatus 3 via the signal line 2f.

A release button 13 is provided at the operation portion 2a of the endoscope 2. The release button 13 is a button to be pressed when the inspector records an endoscope image. When the release button 13 is pressed, a release button operation signal is inputted to the processor 5, the processor 5 generates a release signal and supplies the release signal to the recording apparatus 3. An endoscope image when the release button 13 is pressed is also recorded in a memory 22 of the recording apparatus 3, which will be described later.

The recording apparatus 3 includes a central processing unit (hereinafter referred to as "CPU") 21, the memory 22, a display interface (hereinafter abbreviated as "display I/F") 23, an image capturing section 24, a position/direction detection section 25 and a drive circuit 26. The CPU 21, the memory 22, the display interface (hereinafter abbreviated as "display I/F") 23, the image capturing section 24, the position/direction detection section 25 and the drive circuit 26 are mutually connected via a bus 27.

The CPU 21 is a control section that controls processing of each part in the recording apparatus 3.

The memory 22 is a storage section including a ROM, a RAM, a flash memory or the like, stores various processing programs and various kinds of data executed by the CPU 21 and moreover, as will be described later, the memory 22 also stores endoscope image information and information on the position and the direction or the like. The RAM of the memory 22 stores image data of a plurality of endoscope images captured by the image pickup device 11.

The memory 22 also stores data of a model image of an organ (hereinafter referred to as "organ model image"), which will be described later, and as will be described later, an endoscope image is pasted onto the organ model image. Details will be described later, but the CPU 21 performs a process of pasting an endoscope image onto the model image stored in advance based on the position/direction information of the distal end portion 2d when the endoscope image is captured and stores the organ model image with the endoscope image pasted thereto in the memory 22. The organ model image stored in the memory 22 is used as part of a clinical record.

The organ model image stored in the memory 22 is outputted via the display I/F 23 and displayed on the screen of the monitor 6.

The processor 5 is also connected to the monitor 6. The monitor 6 has a PinP (Picture In Picture) function and can display, together with the organ model image to which the endoscope image is pasted by the CPU 21, a live endoscope image captured by the image pickup device 11 of the endoscope 2.

The image capturing section 24 is a processing section that captures images obtained by the processor 5 in a certain cycle. For example, 30 endoscope images per second, the same as the frame rate, are acquired from the endoscope 2 from the processor 5. Furthermore, the image capturing section 24 also receives a release signal from the processor 5. Note that although the image capturing section 24 captures 30 endoscope images per second, it may also be possible to acquire endoscope images in a longer cycle such as 3 endoscope images per second, which is different from the frame rate.

The position/direction detection section 25 controls the drive circuit 26 that drives the magnetic field generating apparatus 7, causes the magnetic field generating apparatus 7 to generate a predetermined magnetic field, detects, by the magnetic sensor 12, the magnetic field, and generates data of position coordinates (x,y,z) and orientation (that is, Euler angle ($\phi,\theta,\psi$)) of the objective optical window 11a from the detection signal of the detected magnetic field, that is, position/direction information in real time. That is, the position/direction detection section 25 constitutes a position information acquiring section that acquires the position information and direction information from the magnetic sensor 12 and acquires position information of the objective optical window 11a.

The CPU 21 associates the image captured by the image capturing section 24 with information on the position and the direction of the distal end portion 2d calculated from the position/direction information detected by the position/direction detection section 25 and stores the associated image and information in the memory 22.

The CPU 21 further includes a stereo measuring function which is a function that measures a distance from two frame images obtained by image pickup to each part of a target region in the frame image. More specifically, the CPU 21 acquires image pickup position information of the objective optical window 11a based on the position/direction information from the position/direction detection section 25 when two frame images are picked up, and can calculate a distance from the objective optical window 11a to each part in the frame images from a parallax when the two frame images are picked up. A program for the stereo measuring function is stored in the memory 22, and the CPU 21 can perform stereo measurement by reading and executing the program.

The light source apparatus 4 is a light source apparatus that can emit normal light for a normal-light observation mode and special light for a special-light observation mode, and emits either normal light or special light according to the state of the change-over switch 5a for switching between observation modes provided in the processor 5 as illuminating light.

Here, the special-light observation mode is a narrow-band observation mode. Note that the special-light observation mode may be an infrared light observation mode or a fluorescence observation mode. Thus, the endoscope system 1 has two observation modes; the normal-light observation mode and the special-light observation mode, the light source apparatus 4 emits normal illuminating light when the change-over switch 5a is in the normal-light observation mode and emits narrow-band illuminating light having a predetermined wavelength when the change-over switch 5a is in the special-light observation mode. That is, the light source apparatus 4 constitutes an illumination section that radiates white color light or special light having a predetermined wavelength band onto the subject in a manner switchable therebetween.

Thus, the processor 5 generates, in the normal-light observation mode, a normal-light observation image of an object obtained by radiating white color light onto the object, and generates, in the special-light observation mode, a special-light observation image of the object obtained by radiating special light (here, narrow-band light) onto the object.

Note that the narrow-band observation image which is the special-light observation image can also be acquired by applying spectral estimation processing to each image of RGB obtained by radiation of normal light, and therefore the processor 5 may also generate a narrow-band observation image through spectral estimation in the narrow-band observation mode.

(Process of Pasting Endoscope Image to Organ Model Image)

Figure 3:
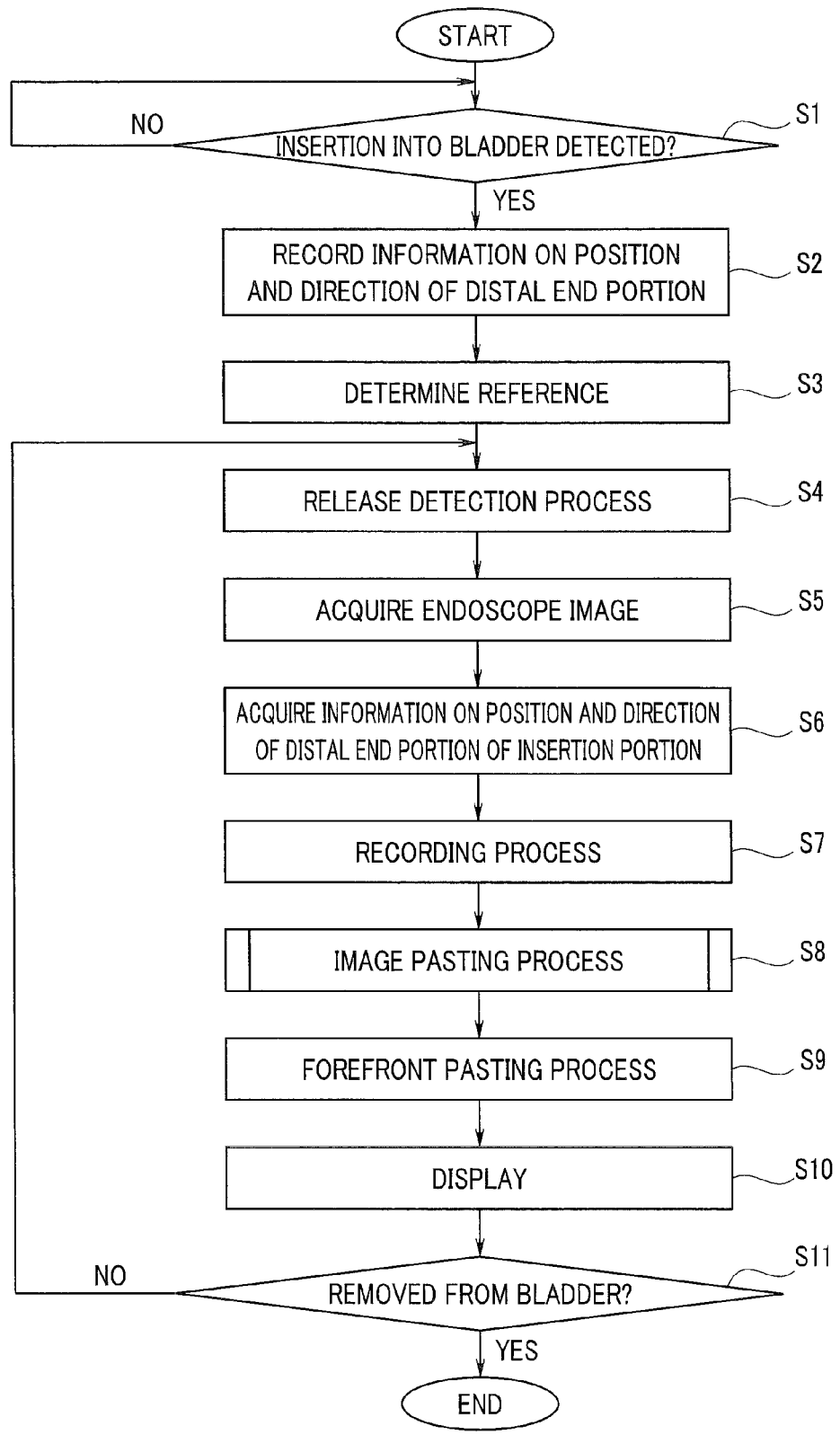
FIG. 3 is a flowchart illustrating a flow example of a process of pasting an endoscope image to a bladder model image during observation of an interior of the bladder according to the embodiment of the present invention.

FIG. 3 is a flowchart illustrating a flow example of a process of pasting an endoscope image to a bladder model image during observation of the interior of the bladder. The process in FIG. 3 is executed after the CPU 21 reads and executes a predetermined program stored in the memory 22 and the inspector inserts the distal end portion 2d of the insertion portion 2b into the urethra.

The CPU 21 determines whether or not insertion of the distal end portion 2d into the bladder B is detected (S1). The distal end portion 2d of the insertion portion 2b is inserted into the urethra and enters the bladder B through the urethra. The insertion of the distal end portion 2d into the bladder B is detected based on the amount of change in luminance of the endoscope image acquired by the image capturing section 24 (average luminance of the whole endoscope image or average luminance of a predetermined partial region of the endoscope image). That is, the CPU 21 makes a determination in S1 taking advantage of the fact that luminance of the endoscope image changes when the distal end portion 2d enters the bladder B from the urethra. When the luminance value of the endoscope image changes from high to low, the CPU 21 determines that the distal end portion 2d enters the bladder B.

Note that the insertion of the distal end portion 2d into the bladder B is detected based on the luminance of the endoscope image, but the detection may also be performed based on the amount of change in color or the amount of change in texture of the endoscope image. For example, the change in color is a change from a red-based color to another color, and the change in texture is a change from a state of image in which a pattern of blood vessel or the like cannot be recognized to a state of image in which a pattern of blood vessel or the like can be recognized.

When the insertion into the bladder B is detected (S1: YES), the position/direction information of the position/direction detection section 25 at the time of detection is recorded as reference information of the position and the direction of the distal end portion 2d (more specifically, objective optical window 11a) (S2).

The CPU 21 makes a reference determination whereby the position and the direction of the distal end portion 2d recorded in S2 are determined respectively as a reference position and a reference direction of the three-dimensional bladder model (hereinafter referred to as "3D bladder model) M1 (S3). Through the process in S3, the CPU 21 can perform transformation from a first coordinate system $(X_0 Y_0 Z_0)$ based on the magnetic field generating apparatus 7 into a coordinate system $(X_1 Y_1 Z_1)$ based on the entrance (neck) of the bladder B and transformation from the coordinate system $(X_1 Y_1 Z_1)$ into a coordinate system $(X_2 Y_2 Z_2)$ based on the center of the bladder model M1. Transformation of the coordinate systems will be described later.

Thus, the processes from S1 to S3 constitute an alignment section that aligns the position of the objective optical window 11a with the position in the coordinate system of a predetermined organ model image in the patient P based on the amount of change of a subject internal image information in the patient P who is the subject.

An inspection of the bladder B is performed while the patient lays on his/her back with the bladder B filled with a predetermined liquid (e.g., physiological salt solution). For example, in the case of an adult, there may be a difference in the size of the bladder B but there is not a significant difference, and the bladder B can be modeled by a spherical shape having substantially the same size.

Figure 4:
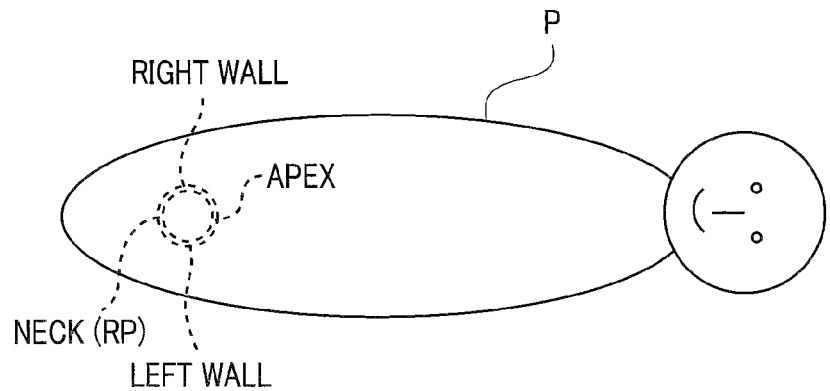
FIG. 4 is a diagram schematically illustrating a position of a patient's bladder for describing names of parts of the bladder according to the embodiment of the present invention.
Figure 5:
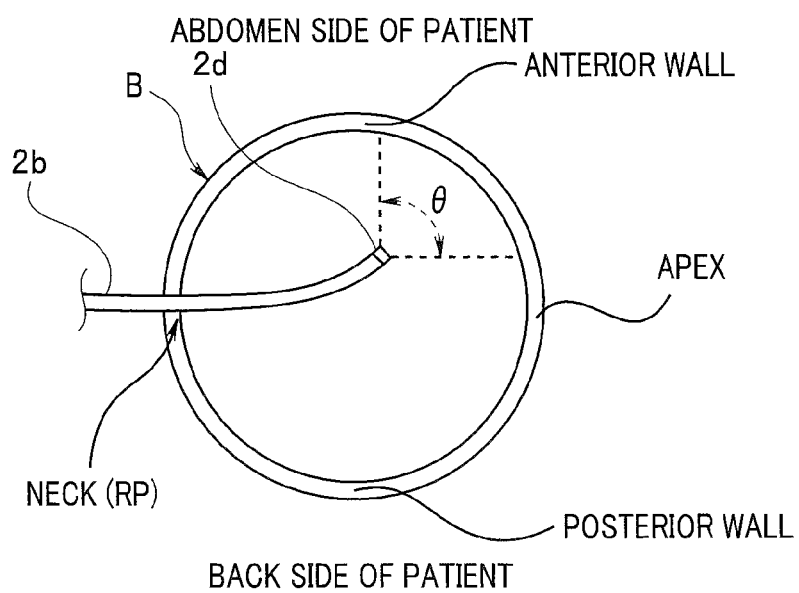
FIG. 5 is a diagram schematically illustrating the bladder for describing names of parts of the bladder according to the embodiment of the present invention.

FIG. 4 is a diagram schematically illustrating the position of the patient's bladder to describe names of parts of the bladder. FIG. 4 is a diagram seen from a direction opposite to the front of the patient P. FIG. 5 is a diagram schematically illustrating the bladder for describing names of parts of the bladder. FIG. 5 is a diagram seen from the left side of the patient P.

The bladder B is divided into a plurality of regions such as a neck RP which is an entrance of the bladder B which is the opening of the urethra, an apex opposed to the neck RP, an anterior wall on the abdomen side, a posterior wall on the back side, a right wall which is on the right side seen from the patient P and a left wall which is on the left side seen from the patient P. Since an inspection of the bladder B is performed while the patient P lays on his/her back with the bladder B filled with a predetermined liquid, it is easy for the inspector to understand the position and the direction of the actual bladder B.

Returning to FIG. 3, when the insertion of the distal end portion 2d into the bladder B is not detected (S1: NO), the process repeats the process in S1. When the insertion of the distal end portion 2d into the bladder B is detected (S1: YES), the distal end portion 2d is located at the position of the neck RP of the bladder B. The magnetic sensor 12 generates 6-axis, that is, (position coordinates (x,y,z) and orientation (Euler angle $(\phi, \theta, \psi)$)) position/direction information, and therefore the recording apparatus 3 records the position and the direction when the insertion of the distal end portion 2d into the bladder B is detected, designates the recorded position and direction as a reference position and a reference direction of the objective optical window 11a for the 3D bladder model M1, and can thereby align the reference position and the reference direction with the position and the direction of the neck RP in the 3D bladder model M1.

As shown in FIG. 5, the image pickup device 11 provided at the distal end portion 2d of the insertion portion 2b picks up an endoscope image with a view angle θ in the bladder B.

Figure 6:
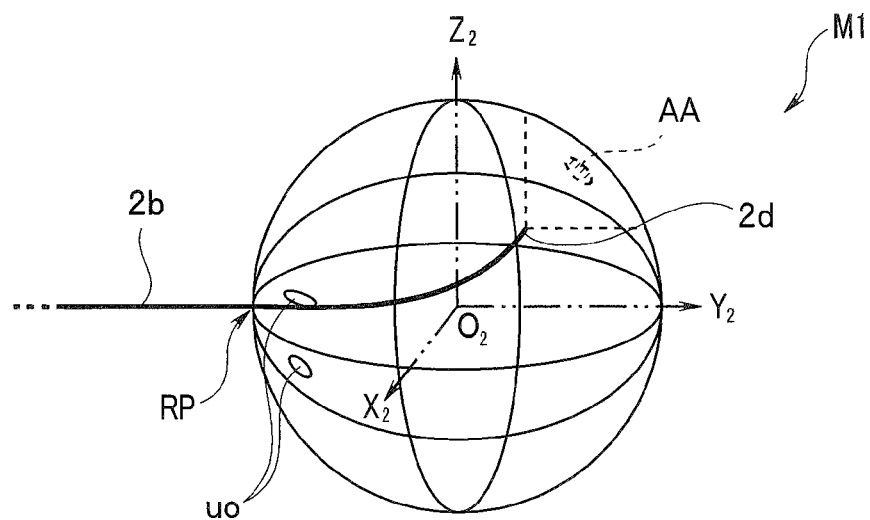
FIG. 6 is a diagram illustrating a 3D bladder model M1 according to the embodiment of the present invention.

FIG. 6 is a diagram illustrating the 3D bladder model M1. The 3D bladder model M1 has a substantially spherical shape and is formed in the three-dimensional coordinate system $X_2 Y_2 Z_2$. The coordinate system $X_2 Y_2 Z_2$ is a coordinate system transformed from the coordinate system $X_1 Y_1 Z_1$. Note that FIG. 6 also shows a graphic of the insertion portion 2b to show the neck RP which is the entrance of the insertion portion 2b in the bladder B together.

The 3D bladder model M1 is formed assuming an axis passing through the center O of the sphere in a direction from the right wall to the left wall as an $X_2$ axis, an axis passing through the center O of the sphere in a direction from the neck to the apex as a $Y_2$ axis and an axis passing through the center O of the sphere in a direction from the posterior wall to the anterior wall as a $Z_2$ axis.

Figure 7:
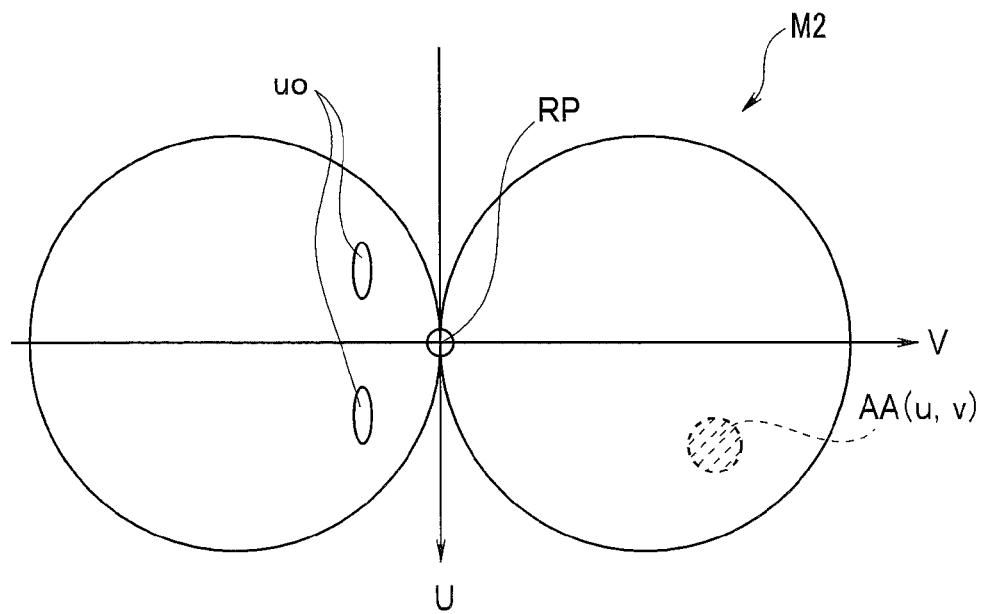
FIG. 7 is a diagram illustrating a two-dimensional model M2 of a bladder B according to the embodiment of the present invention.
Figure 8:
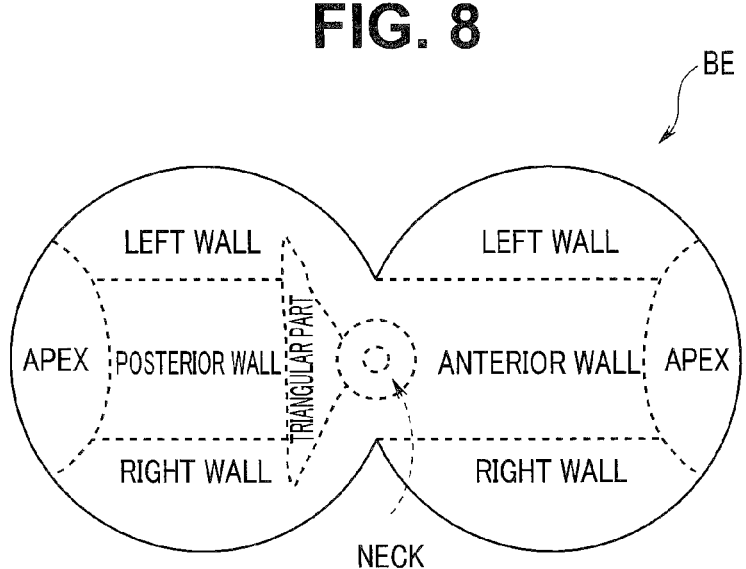
FIG. 8 is a diagram illustrating a developed view of the bladder BE.

FIG. 7 is a diagram illustrating a two-dimensional model (hereinafter referred to as "2D bladder model") M2 of the bladder B. The 2D bladder model M2 has a shape including two circles and is formed in a two-dimensional coordinate system UV. The 2D bladder model M2 has substantially the same shape as that of a developed view of the bladder (schema) BE shown in FIG. 8. FIG. 8 is a diagram illustrating the developed view of the bladder BE. The developed view of the bladder BE is a diagram illustrating the position of each part in the bladder B, and as shown in FIG. 8, each part in the bladder B corresponds to each predetermined region on the developed view of the bladder BE.

Two ureteral orifices of the bladder B are located at positions shown by uo in FIG. 6 and FIG. 7. For example, in FIG. 6, when a lesioned part AA exists at a position shown by a dotted line in the bladder B, the position of the lesioned part AA in FIG. 6 corresponds to a position shown by a dotted line in FIG. 7.

Returning to FIG. 3 again, the information on the position and the direction of the distal end portion 2d when the insertion of the distal end portion 2d into the bladder B is detected is recorded as reference information in S2 and a reference of the 3D bladder model M1 and a reference of the 2D bladder model M2 are derived from the position and the direction specified by the reference information.

Next, the CPU 21 performs a release detection process (S4). This release detection process is a process of detecting whether or not the release button 13 of the operation portion 2a of the endoscope 2 is pressed. When the release button 13 is pressed, a release signal is inputted to the image capturing section 24 via the processor 5. The CPU 21 monitors a rise (or fall) of the release signal inputted to the image capturing section 24, and can thereby detect whether or not the release button 13 is pressed.

The CPU 21 acquires an endoscope image from the image capturing section 24 (S5). As described above, the image capturing section 24 acquires an endoscope image from the processor 5 every 1/30 second, which is the same as the frame rate.

The CPU 21 acquires information on the position and the direction of the distal end portion 2d of the insertion portion 2b (S6). By reading the position/direction information from the position/direction detection section 25, the CPU 21 can acquire the information on the position and the direction of the distal end portion 2d.

Furthermore, in S6, the CPU 21 converts the position/direction information in the coordinate system $(X_0Y_0Z_0)$ to the position/direction information in the three-dimensional coordinate system $(X_2Y_2Z_2)$ based on the reference information determined in S3. That is, in S1 to S3, after the position information of the objective optical window 11a is caused to match the coordinate system of the bladder model image which is a predetermined organ model image, in S6, the position and the direction of the distal end portion 2d acquired in the position/direction detection section 25 (that is, the position and the direction of the objective optical window 11a) are associated with the position and the direction in the coordinate system of the bladder model image. That is, the process in S6 constitutes an association section that associates the position information recorded in the memory 22 which is the storage section with the model image of the predetermined organ in the subject.

The CPU 21 executes a recording process of recording the endoscope image, the position and the direction on the 2D model image and the presence or absence of a release signal in the memory 22 (S7). That is, the process in S7 constitutes a recording section that records the endoscope image which is the subject internal image acquired by the image pickup device 11 in association with the position information and the direction information acquired by the position/direction detection section 25.

Next, the CPU 21 executes an image pasting process (S8). The image pasting process is a process of pasting the endoscope image to be pasted onto the inner surface of the 3D bladder model M1 which is a sphere onto the figure of the 2D model M2 (hereinafter referred to as "2D model image") based on the position/direction information acquired in S6 and converted to the three-dimensional coordinate system $(X_2Y_2Z_2)$. That is, the process in S8 constitutes an image pasting section that pastes the subject internal image onto the model image of the predetermined organ associated in S6 based on the position information. In the image pasting processing in S8, when there are a plurality of images pasted at the same position, an unblurred and clear endoscope image is selected from among those images and the image is pasted onto the 2D model image so that that image comes to the forefront. The image pasting process in S8 will be described later.

Here, in S7, all the subject internal images acquired from the image pickup device 11 are recorded in the memory 22 in association with the position information, and in S8, all the subject images recorded in the memory 22 and the position information associated with each subject internal image are read and it is determined whether or not the subject internal image is an image that can be pasted.

That is, the process in S8 constitutes an image generation section that generates an image in which the subject internal image is pasted onto the model image of the predetermined organ in which the position of the objective optical window 11a and the position of the 3D model image in the coordinate system are associated with each other in S1 to S3 that constitute the alignment section. The pasting process in S8 is performed by pasting the endoscope image projected onto the inner surface of the sphere of the 3D bladder model M1 defined by the three-dimensional coordinate system $(X_2Y_2Z_2)$ at a position on the image of the 2D bladder model M2 of the two-dimensional coordinate system (U,V).

The position and the direction of the endoscope image pasted onto the image of the 2D bladder model M2 are determined as described above and the size of the endoscope image pasted is changed according to, for example, the distance between the distal end portion 2d and the image pickup region of the bladder B.

The reference information on the position and the direction determined in S3 is the position and the direction in the three-dimensional coordinate system $(X_0Y_0Z_0)$ determined based on the magnetic field generating apparatus 7 outside the body and the position and the direction in the image pasting process in S8 are a position and a direction in the two-dimensional coordinate system (U,V) based on the neck RP of the 2D bladder model M2.

Thus, the CPU 21 derives the position/direction information of the distal end portion 2d in the two-dimensional coordinate system from the reference information obtained in S3 and calculates the position and a gradient at which the endoscope image is projected and pasted onto the 2D model image based on the derived position/direction information.

When an endoscope image is already pasted at the position at which the endoscope image is to be pasted, image pasting in S8 is performed such that the image acquired later is pasted so as to be superimposed on the previously acquired and pasted endoscope image.

Figure 9:
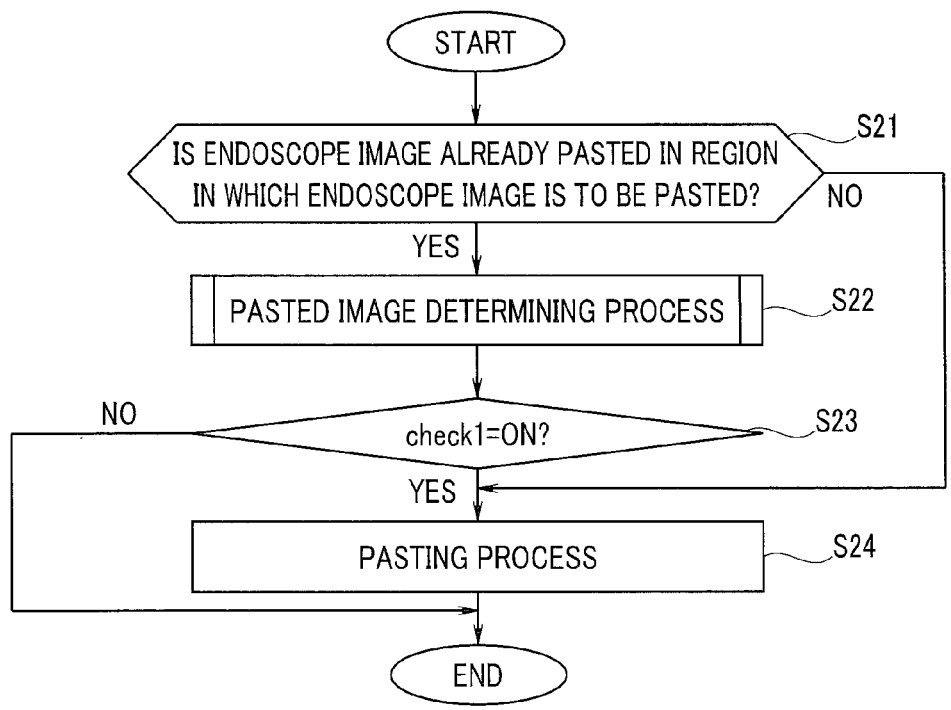
FIG. 9 is a flowchart illustrating a flow example of the image pasting process in S8.

FIG. 9 is a flowchart illustrating a flow example of the image pasting process in S8.

First, the CPU 21 determines whether or not an endoscope image has already been pasted in the region in which the endoscope image is to be pasted (S21). This determination is made based on whether or not the region in which the endoscope image acquired in S5 is to be pasted has any region overlapping with the already pasted endoscope image.

When an endoscope image is already pasted in the region in which the endoscope image is to be pasted (S21: YES), the CPU 21 executes a pasting image determining process (S22).

Figure 10:
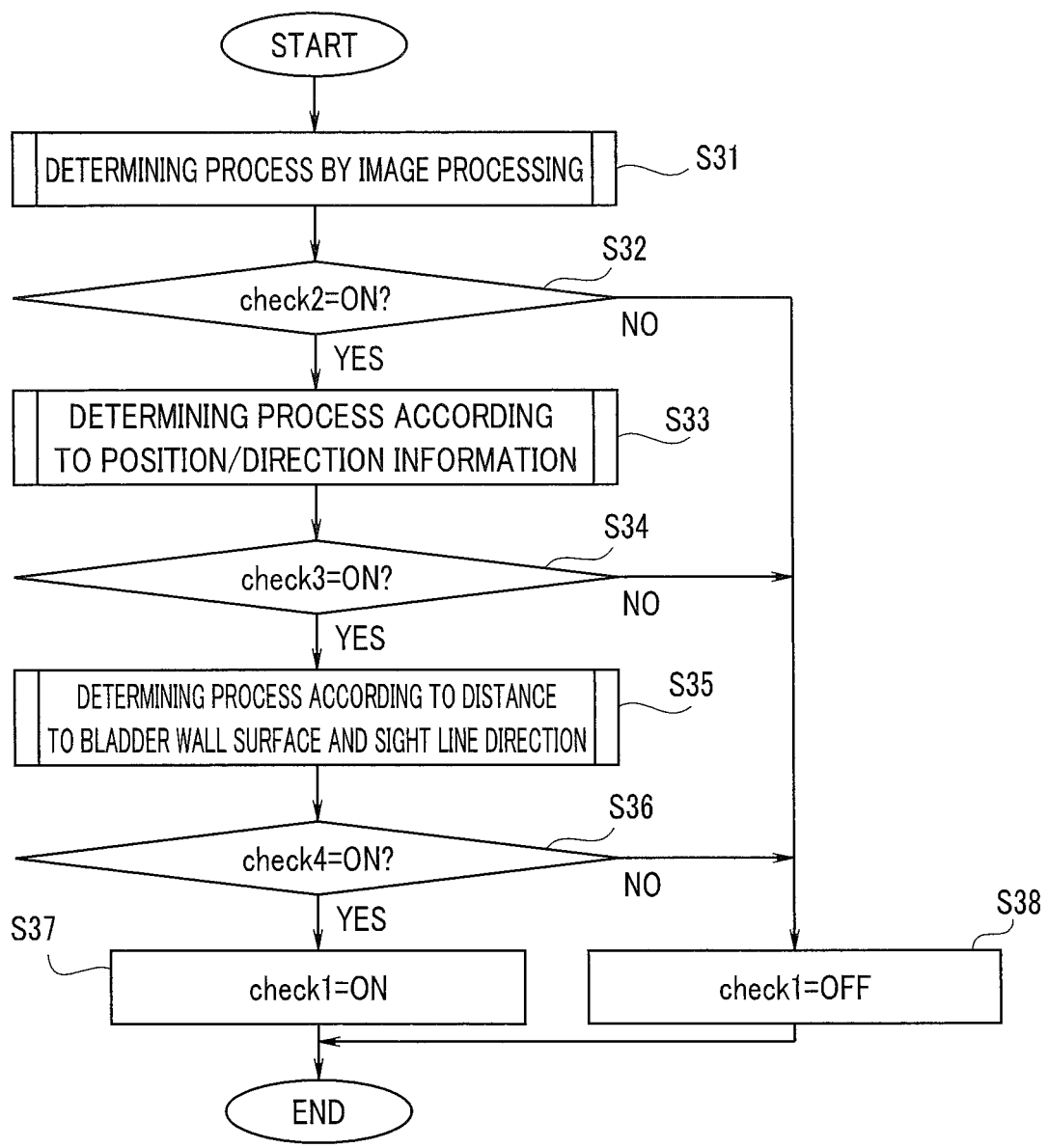
FIG. 10 is a flowchart illustrating a flow example of a pasted image determining process in S22.

FIG. 10 is a flowchart illustrating a flow example of the pasting image determining process in S22. Note that the process in FIG. 10 includes a process that can be executed based on information of only one endoscope image acquired in S5 and a process that is executed using information of a plurality of endoscope images including the already acquired image, and therefore when all necessary information on each endoscope image is available, each process in FIG. 10 about each endoscope image is executed.

The CPU 21 first executes a determining process through image processing (S31) to determine whether or not check2 which is determination information of the image processing is ON (S32). The determining process through image processing will be described later using FIG. 11. If check2 is ON, the CPU 21 executes the determining process according to position/direction information (S33). That is, the determining process in S22 includes a determining process as to whether or not to perform pasting based on image information of a subject internal image obtained through image processing on the subject internal image acquired by the image pickup device 11.

After the process in S33, the CPU 21 determines whether or not the determination information check3 which is the determination information of the position/direction information is ON (S34). The determining process using the position/direction information will be described later using FIG. 12. When the determination information check3 is ON, the CPU 21 performs the determining process according to the distance to the bladder wall surface and the sight line direction (S35).

After the process in S36, the CPU 21 determines whether or not a determination information check4 which is determination information according to the distance to the bladder wall surface and the sight line direction is ON (S36). The determining process according to the distance to the bladder wall surface and the sight line direction will be described later using FIG. 13.

When the determination information check4 is ON in S36 (S36: YES), the CPU 21 turns ON the determination information check1 (S37). That is, when the determination information check2, check3 and check4 of all the determination results in S31, S33 and S35 are ON, the determination information check1 is turned ON. In other words, in any one of S31, S33 and S35, if any one of the determination information check2, check3 and check4 is OFF (S32: NO, S34: NO, S36: NO), the CPU 21 turns OFF the determination information check1 (S38).

As described above, the process in S22 constitutes a determining section that determines whether or not to perform pasting in the image pasting process based on the image information or position information of the subject internal image acquired by the image pickup device 11.

Returning to FIG. 9, after the process in S22, the CPU 21 determines whether or not the determination information check1 is ON about the endoscope image for which the determination result of the determination infatuation check1 is obtained (S23). When the determination information check1 is ON (S23: YES), the CPU 21 performs the pasting process. As a result, the endoscope image whose determination information check1 is ON is projected and pasted onto the 2D model image. When the determination information check1 is not ON (S23: NO), the CPU 21 does not perform the pasting process.

Figure 11:
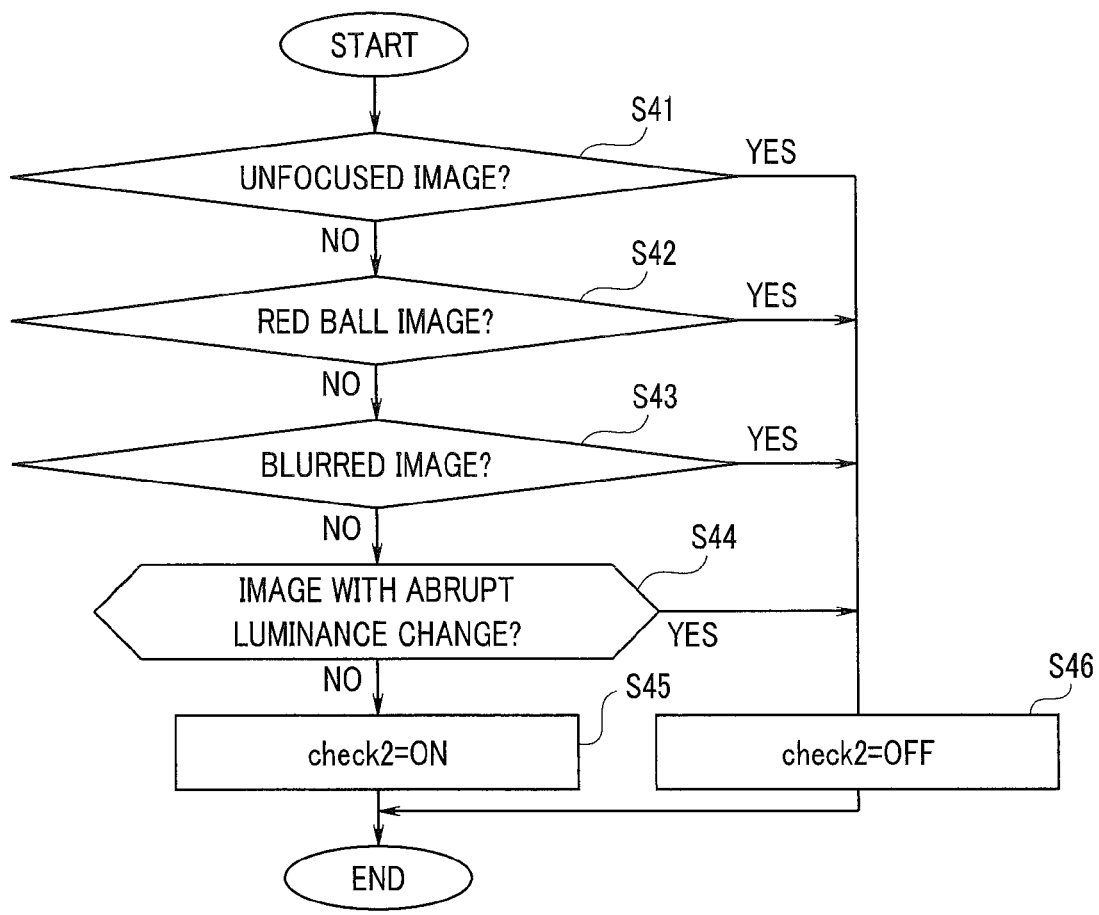
FIG. 11 is a flowchart illustrating a flow example of the determining process through image processing in S31.

FIG. 11 is a flowchart illustrating a flow example of the determining process through the image processing in S31. First, the CPU 21 determines whether or not the endoscope image acquired in S5 is an unfocused image (S41). Whether or not the endoscope image is an unfocused image can be determined based on an edge component in the endoscope image.

When the endoscope image is not an unfocused image (S41: NO), the CPU 21 determines whether or not the acquired endoscope image is a red ball image (S42). Whether or not the endoscope image is a red ball image can be determined based on a pixel value of an R pixel in the endoscope image.

When the endoscope image is not a red ball image (S42: NO), the CPU 21 determines whether or not the acquired endoscope image is a blurred image (S43). Whether or not the endoscope image is a blurred image can be determined based on the edge component in the endoscope image.

When the endoscope image is not a blurred image (S43: NO), the CPU 21 determines whether or not the acquired endoscope image includes a part with an abrupt luminance change (S44). Whether or not the endoscope image includes a part with an abrupt luminance change can be determined based on a distribution of the luminance value in the endoscope image. The case where the endoscope image includes a part with an abrupt luminance change means, for example, a case where the distal end portion 2d is not oriented toward the bladder wall surface at an appropriate angle.

When there is no part with an abrupt luminance change in the endoscope image (S44: NO), the CPU 21 turns ON the determination information check2 (S45). When the endoscope image is an unfocused image (S41: YES), a red ball image (S42: YES), or a blurred image (S43: YES) or when the endoscope image includes a part with an abrupt luminance change (S44: YES), the CPU 21 turns OFF the determination information check2 (S46).

That is, the image processing causes the determination information check2 to be turned OFF for an unclear endoscope image such as an unfocused image.

Figure 12:
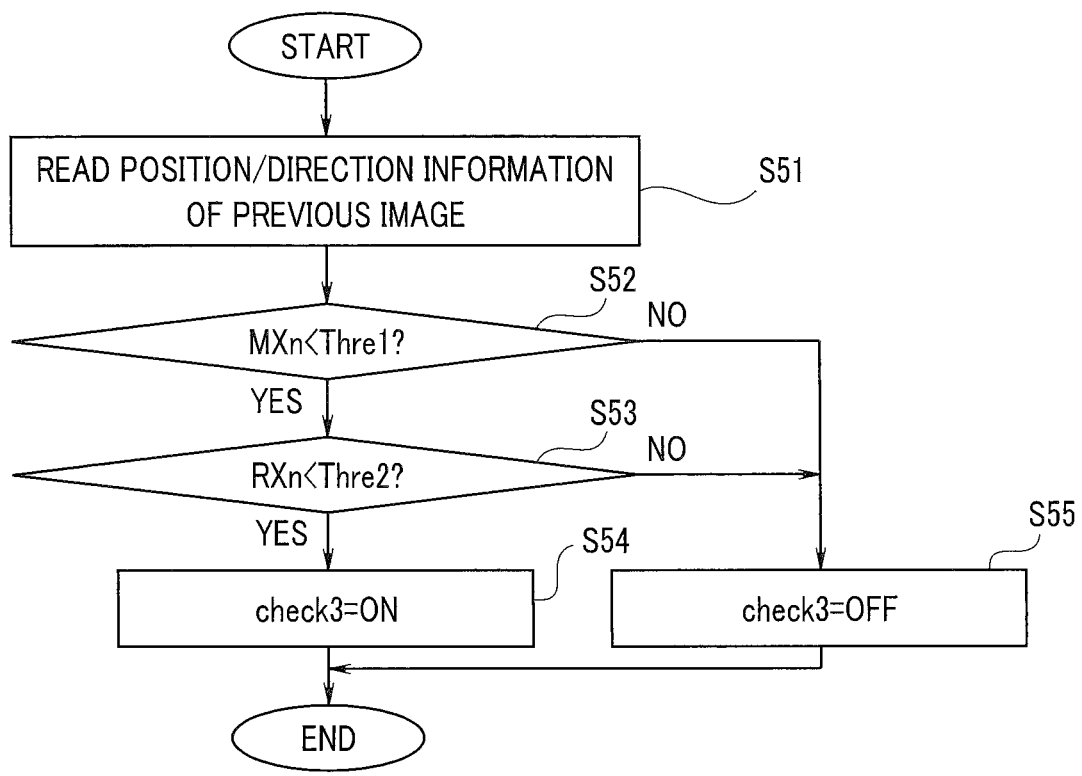
FIG. 12 is a flowchart illustrating a flow example of the determining process according to position/direction information in S33.

FIG. 12 is a flowchart illustrating a flow example of the determining process according to the position/direction information in S33. First, the CPU 21 reads position/direction information of a previous image (S51). Here, the position/direction information of the previous image is position/direction information about two frames acquired before the frame acquired in S5.

Note that when the image pasting determining process is performed at a time interval lower than the frame rate such as 3 frames per second, the image capturing section 24 captures an endoscope image at the same rate as the frame rate and reads position/direction information of frames before and after the frame of the endoscope image subject to the image pasting determination in S51.

When the p-th frame acquired in S5 is the latest endoscope image Img (P), the position/direction information on two endoscope images Img(p−2) and Img(p−1) acquired before the frame is already acquired, and therefore the two pieces of position/direction information are read.

Note that with regard to the first endoscope image, there are no two frames earlier than that image, and with regard to the subsequent second endoscope image, there are no two frames earlier than that image. Thus, the process in S8 is executed on the endoscope image Img(p−1) immediately preceding the latest endoscope image Img(p) after the third and subsequent endoscope images are acquired.

Next, the CPU 21 determines whether or not a moving speed $MX_n$ of the distal end portion 2d is less than a predetermined threshold Thre1 (S52). Here, when n is (p−2) and m is p, $MX_n$ is expressed by the following Equation (1).

$$MX_n = \frac{\sqrt{(X_n - X_m)^2 + (Y_n - Y_m)^2 + (Z_n - Z_m)^2}}{(T_n - T_m)} \quad \text{Equation (1)}$$

In Equation (1), $x_n$, $y_n$, $z_n$, $x_m$, $y_m$ and $z_m$ are position information in the three-dimensional coordinate system $(X_2Y_2Z_2)$, and $T_n$ and $T_m$ are a time at which the endoscope image Img(p−2) is acquired and a time at which the endoscope image Img(p) is acquired.

That is, it is determined from the position information of the distal end portion 2d whether or not the image pickup device 11 is moving at a predetermined speed or higher, and if the endoscope image Img(p−1) is an image when the distal end portion 2d is not moving at a predetermined speed or higher (that is, if the endoscope image Img(p−1) is an image picked up when the moving speed $MX_n$ of the distal end portion 2d is less than the predetermined threshold Thre1), the determination in S52 is YES and if the endoscope image Img(p−1) is an image when the distal end portion 2d is moving at a speed less than the predetermined speed (that is, if the endoscope image Img(p−1) is an image picked up when the moving speed $MX_n$ of the distal end portion 2d is equal to or higher than the predetermined threshold Thre1), the determination in S52 is NO.

Thus, the determining process in S22 includes a determining process as to whether or not to perform pasting based on the moving distance of the objective optical window 11a calculated from the position information.

Next, the CPU 21 determines whether or not an angular velocity $RX_n$ around the axis of the distal end portion 2d is less than a predetermined threshold Thre2 (S53). Here, when n is (p−2) and m is p, $RX_n$ is expressed by the following Equation (2).

$$RX_n = \frac{|\gamma_n - \gamma_m|}{(T_n - T_m)} \quad \text{Equation (2)}$$

In Equation (2), $\gamma_n$ and $\gamma_m$ are angles around the axis of the distal end portion 2d in the three-dimensional coordinate system $(X_2Y_2Z_2)$.

Note that when the magnetic sensor 12 is a 5-axis sensor, the determining process in S53 is omitted.

That is, it is determined whether or not the angular velocity around the axis of the distal end portion 2d is rotating at a predetermined angular velocity or higher, and if the endoscope image Img(p−1) is an image when the distal end portion 2d is not rotating at the predetermined angular velocity or higher (that is, if the endoscope image Img(p−1) is an image picked up when the angular velocity $RX_n$ around the axis of the distal end portion 2d is less than the predetermined threshold Thre2), the determination in S53 is YES, and if the endoscope image Img(p−1) is an image when the distal end portion 2d is rotating at a speed less than the predetermined angular velocity (that is, if the endoscope image Img(p−1) is an image picked up when the angular velocity $RX_n$ around the axis of the distal end portion 2d is equal to or higher than the predetermined threshold Thre2), the determination in S53 is NO.

Thus, the determining process in S22 includes a determining process as to whether or not to perform pasting based on the angle information of the objective optical window 11a calculated from the position information.

When the determination in S53 is YES (that is, when the moving speed of the distal end portion 2d is less than a predetermined speed and the angular velocity around the axis of the distal end portion 2d is less than a predetermined angular velocity), the CPU 21 turns ON the determination information check3 (S54). When the moving speed of the distal end portion 2d is equal to or higher than a predetermined speed (S52: NO), or when the angular velocity around the axis of the distal end portion 2d is equal to or higher than the predetermined angular velocity (S53: NO), the CPU 21 turns OFF the determination information check3 (S55).

Figure 13:
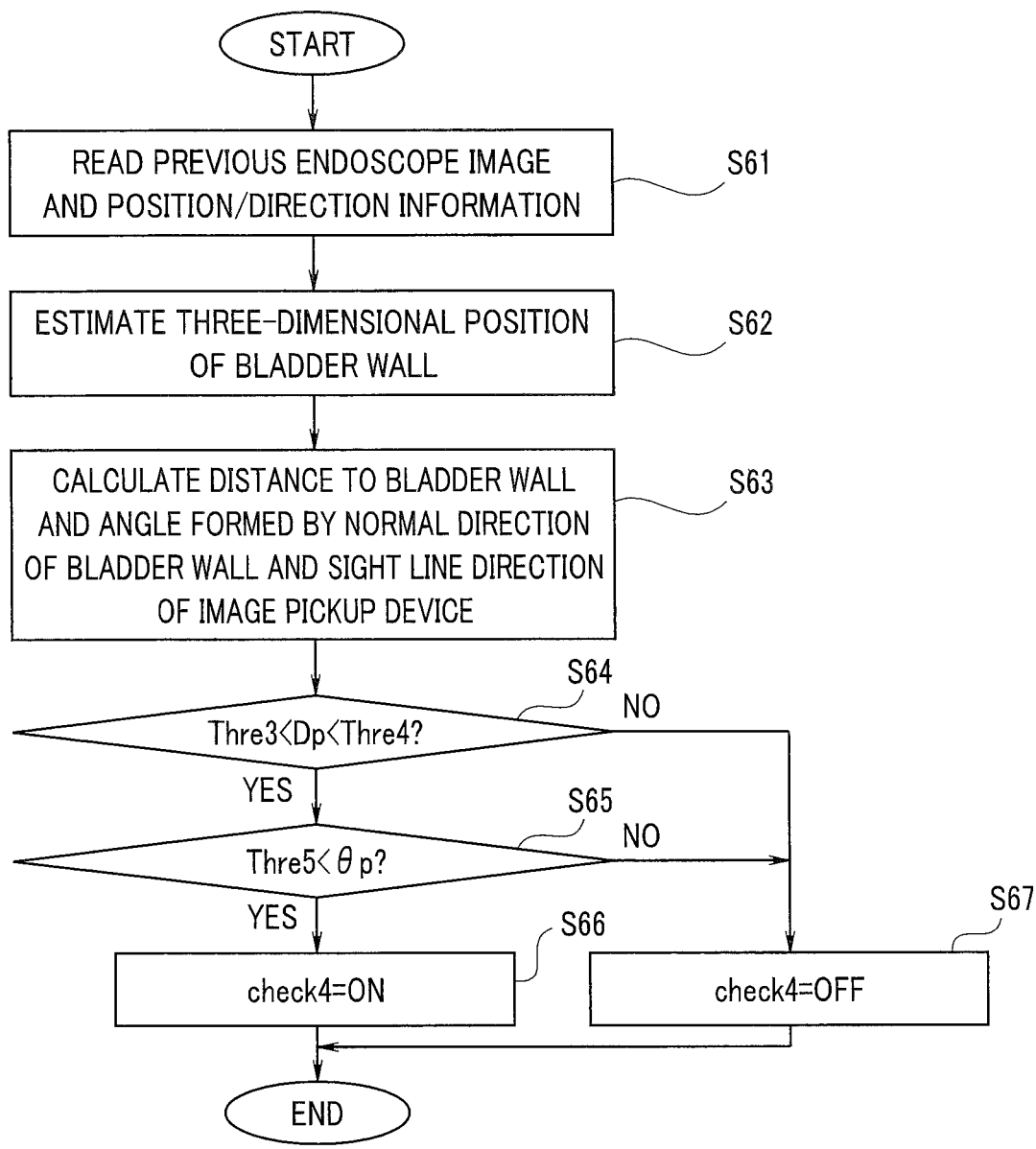
FIG. 13 is a flowchart illustrating a flow example of the determining process according to a distance to a bladder wall and a sight line direction in S35.

FIG. 13 is a flowchart illustrating a flow example of the determining process according to the distance to the bladder wall and the sight line direction in S35. First, the CPU 21 reads the previous endoscope image and the latest position/direction information of the distal end portion 2d (S61).

The previous endoscope image read in S61 is an endoscope image Img(p−k) acquired at a position at a predetermined distance from the position at which the latest endoscope image Img(p) is acquired and the distance from each part or each point in the endoscope image is measured using a stereo measuring function based on two images of the latest endoscope image Img(p) and the previous endoscope image Img(p−k). Here, k is an integer of 1 or more.

Next, the CPU 21 estimates a three-dimensional position of each part or each point of the bladder wall surface (S62). The CPU 21 calculates the distance from the distal end portion 2d to each part or each point of the two endoscope images using the stereo measuring function and estimates the three-dimensional position of each part or each point of the bladder wall surface.

The CPU 21 then calculates a distance Dp to the bladder wall surface obtained by the estimation in S62 and an angle θp formed by the normal direction at a point of the bladder wall surface at the center of the endoscope image and the sight line direction of the image pickup device 1 (S63).

The CPU 21 determines whether or not the distance Dp falls within the predetermined thresholds Thre3 and Thre4 (S64). When the distal end portion 2d is too close to the bladder wall surface or far by a certain degree or more, the endoscope image picked up by the image pickup device 11 may be unfocused or may not have appropriate brightness. Thus, as a range in which images can be picked up with appropriate focus and brightness, a range is set in advance as an appropriate distance to the object, the range in which the distance Dp is greater than the predetermined threshold Thre3 and less than the predetermined threshold Thre4.

Figure 14:
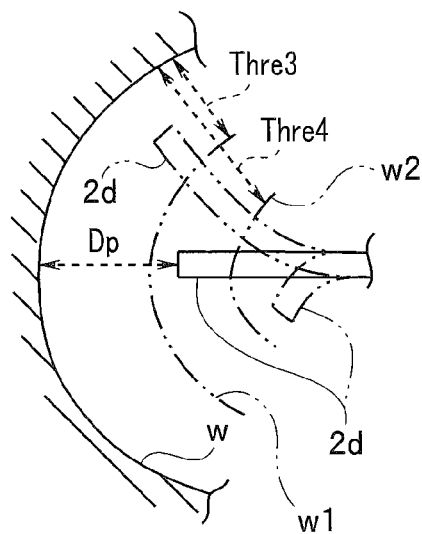
FIG. 14 is a diagram provided for describing a distance Dp between a bladder wall surface and a distal end portion 2d, and a relationship with thresholds Thre3 and Thre4 according to the embodiment of the present invention.

FIG. 14 is a diagram provided for describing a relationship between the distance Dp between the bladder wall surface and the distal end portion 2d, and thresholds Thre3 and Thre4. As in the case of the distal end portion 2d shown by a solid line in FIG. 14, when the distance Dp between the distal end portion 2d and the bladder wall surface w is between the predetermined thresholds Thre3 and Thre4, an appropriate endoscope image is obtained, whereas as shown by two-dot dashed line, when the distance Dp between the distal end portion 2d and the bladder wall surface w is equal to or less than the predetermined threshold Thre3 or equal to or greater than the predetermined threshold Thre4, an appropriate endoscope image cannot be obtained. In FIG. 14, when the distal end portion 2d is located between two-dot dashed lines w1 and w2, an appropriate endoscope image can be obtained.

Thus, the determining process in S22 includes a determining process as to whether or not to perform pasting based on the position information and distance information from the objective optical window 11a to the subject calculated from the subject internal image.

When the distance Dp between the distal end portion 2d and the bladder wall surface w is between the predetermined thresholds Thre3 and Thre4 (S64: YES), the CPU 21 determines whether or not the angle θp formed by the normal direction at a point of the bladder wall surface at the center of the endoscope image and the sight line direction of the image pickup device 11 is less than a predetermined threshold Thre5 (S65).

If an endoscope image picked up when the angle θp formed by the normal direction of the bladder wall surface w and the sight line direction of the image pickup device 11 is less than the predetermined threshold Thre5 is pasted, an image is pasted whose angle θp is substantially constant is pasted.

Figure 15:
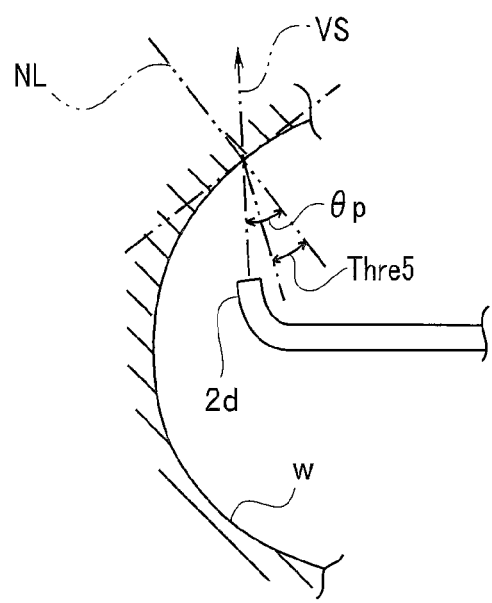
FIG. 15 is a diagram provided for describing an angle formed by a normal direction of the bladder wall surface and a sight line direction of an image pickup device 11 according to the embodiment of the present invention.

FIG. 15 is a diagram provided for describing the angle formed by the normal direction of the bladder wall surface and the sight line direction of the objective optical window 11*a*. As shown in FIG. 15, when the angle θp formed by a sight line direction VS of the distal end portion 2*d* and a normal direction NL of the bladder wall surface w at a center position of the endoscope image is less than the predetermined threshold Thre5, only endoscope images in which the angle θp is less than the predetermined threshold Thre5 are pasted onto the image of the 2D bladder model M2. The normal direction NL of the bladder wall surface w can be calculated from the distance of the bladder wall surface w calculated from the distance of each part or each point of the bladder wall surface w obtained by stereo measurement.

Thus, the determining process in S22 includes a determining process of approximating the surface of the subject based on the position information and subject internal image and determining whether or not to perform pasting based on the angle formed by the normal vector of the surface and the sight line directional vector of the image pickup device 11.

When the angle θp formed by the normal direction NL of the bladder wall surface w and the sight line direction VS of the image pickup device 11 is less than the predetermined threshold Thre5 (S65: YES), the CPU 21 turns ON the determination information check4 (S66).

When the distance Dp between the distal end portion 2*d* and the bladder wall surface w is not between the predetermined thresholds Thre3 and Thre4 (S64: NO) or when the angle θp formed by the normal direction NL of the bladder wall surface w and the sight line direction VS of the image pickup device 11 is equal to or greater than the predetermined threshold Thre5 (S65: NO), the CPU 21 turns OFF the determination information check4 (S67).

The image pasting process is performed as described above. Note that in the above-described example, in S7, an endoscope image and information on the position and the direction are recorded in association with each other in the memory 22, and then the image pasting process in S8 is performed, but the image pasting process in S8 may be executed without recording in the memory 22. That is, the subject image acquired by the image pickup device 11 may not be recorded in the memory 22, but the image pasting process in S8 may directly paste the subject image acquired by the image pickup device 11 onto the model image of the predetermined organ.

Returning to FIG. 3, the CPU 21 then performs a forefront pasting process (S9). When there are a plurality of endoscope images to be pasted onto the 2D model image and all or some endoscope images are pasted so as to overlap with each other, the forefront pasting process is a process intended to ensure that the endoscope image with a release signal is disposed on the forefront without being hidden behind other endoscope images. That is, the subject internal image when the release button 13 of the endoscope 2 is pressed is pasted onto the forefront of the model image of the predetermined organ in preference to other subject internal images.

Note that when all or some of a plurality of endoscope images with release signals overlap with each other in S9, pasting is performed such that the image acquired later is pasted by being superimposed on endoscope images acquired and pasted earlier.

Thus, the process in S9 is performed only on a pixel region where pixels of other already pasted endoscope images are located at pixel positions of the endoscope image pasted in S8.

The CPU 21 displays the 2D model image subjected to the forefront pasting process on the monitor 6 via the display I/F 23 (S10). In this case, the CPU 21 generates also a 3D model image and displays it together with the 2D model image. The CPU 21 generates an image of the insertion portion 2*b* based on the position/direction information of the distal end portion 2*d*, causes the image to be superimposed on the 3D model image and thereby generates a 3D model image.

In S10, the CPU 21 estimates the shape of the insertion portion based on the information on the position and the direction of the distal end portion 2*d* acquired in S6 and generates an image of the insertion portion 2*b* of the estimated shape. Thus, the process in S10 includes a shape estimation section that estimates the shape of the insertion portion 2*b* based on the position information and the direction information of the distal end portion 2*d* acquired in S6 and the position information and the orientation information of the urethral opening RP, and performs, in S10, a process of superimposing an image of the insertion portion which is shape information estimated by the shape estimation section on the 3D model image relating to the predetermined organ.

The CPU 21 determines whether or not the distal end portion 2*d* of the insertion portion 2*b* has been removed from the bladder B (S11). The determination in S11 can be made by determining whether or not the position coordinates of the distal end portion 2*d* are moved from the neck of the bladder B to the inside of the urethra.

When the distal end portion 2*d* is not removed from within the bladder B (S11: NO), the process returns to S4, and the CPU 21 repeats the processes from S4 to S11 until the distal end portion 2*d* is removed from within the bladder B.

Figure 16:
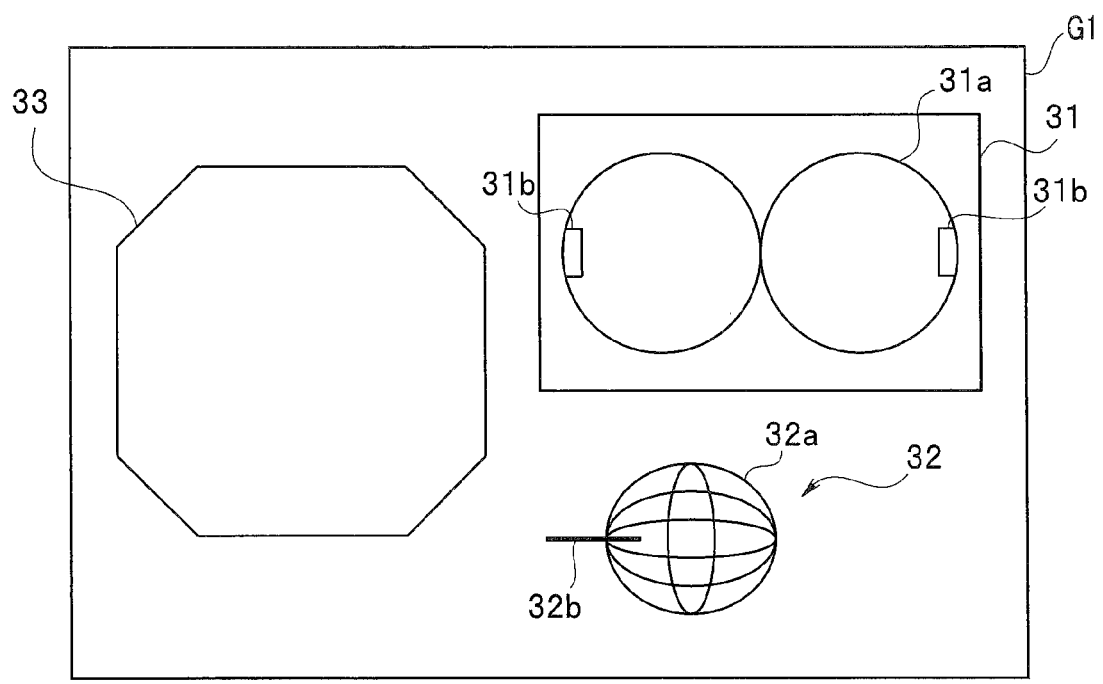
FIG. 16 is a diagram illustrating an example of a display screen during an endoscope inspection displayed on a screen of a monitor 6 according to the embodiment of the present invention.

FIG. 16 is a diagram illustrating an example of the display screen at the time of an endoscope inspection displayed on the screen of the monitor 6. As shown in FIG. 16, a screen G1 is a screen generated by the CPU 21 and includes a 2D model image display section 31, a 3D model image display section 32 and a live image display section 33 that displays a live endoscope image (hereinafter referred to as "live image").

The 2D model image display section 31 is a region for displaying a 2D model image corresponding to the 2D model in FIG. 7. The 2D model image display section 31 displays a 2D model image 31*a* which is a 2D developed view of the bladder and an endoscope image 31*b* which is a subject internal image pasted onto the 2D model image 31*a* through the processes in S7 and S9.

The 3D model image display section 32 is a region for displaying a 3D model image corresponding to a 3D model in FIG. 6. The 3D model image display section 32 displays a 3D model image 32*a* and an insertion portion image 32*b* indicating the position and the direction of the distal end portion 2*d* of the insertion portion 2*b* in the 3D model. The CPU 21 generates the insertion portion image 32*b* based on the current position/direction information on the distal end portion 2*d* as described above.

The 2D model image display section 31 in FIG. 16 displays an image when an endoscope image first picked up while the distal end portion 2d that enters the bladder B is oriented toward the apex direction is pasted onto the 2D model image 31a.

As described above, the live subject internal image acquired by the image pickup device 11 is displayed together with the model image, and further the insertion shape of the insertion portion 2b including the image pickup device 11 that picks up an image of the live subject internal image is also displayed together with the model image.

The live image display section 33 is a region for the monitor 6 to display the endoscope image acquired from the processor 5 as-is. The live image display section 33 is included in a screen G1 by, for example, the PinP function of the monitor 6.

Note that the live endoscope image is displayed on the monitor 6 using the PinP function of the monitor 6 here, but the live image may be synthesized on the screen G1 by the CPU 21 of the recording apparatus 3 and outputted to the monitor 6.

Figure 17:
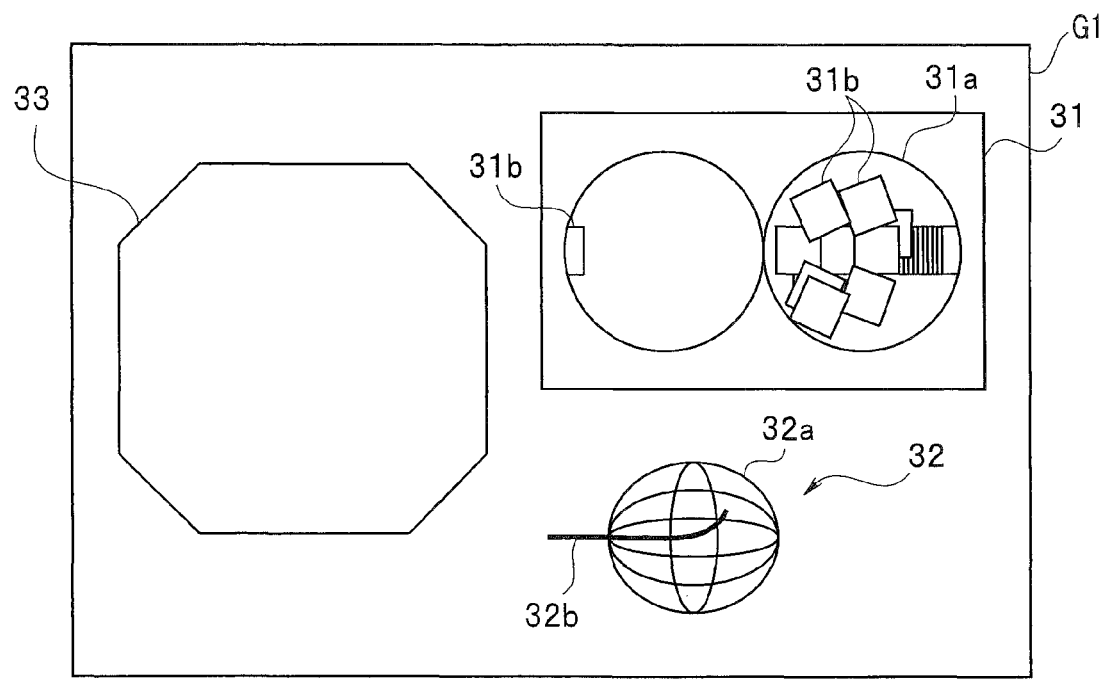
FIG. 17 is a diagram illustrating an example of a display screen displayed on a screen of the monitor 6 with a plurality of endoscope images pasted onto a 2D model image 31a according to the embodiment of the present invention.

FIG. 17 is a diagram illustrating an example of the display screen displayed on the screen of the monitor 6 in which a plurality of endoscope images are pasted onto the 2D model image 31a. The 2D model image display section 31 in FIG. 17 displays an image when a plurality of endoscope images 31b picked up while the distal end portion 2d is moving and is oriented toward various directions are pasted onto the 2D model image 31a. Most of images pasted onto the 2D model image 31a are clear images without unfocused parts or the like in the image pasting process.

The processes from S4 to S11 are repeated in a predetermined cycle (cycle of 1/30 second here), clear images without unfocused parts or the like are thereby superimposed on the plurality of endoscope images acquired in S5 through the pasting process in S8 and the 2D model image display section 31 includes a plurality of endoscope images 31b as shown in FIG. 17. The region where the plurality of endoscope images are pasted is the region observed by the inspector. Thus, the inspector can simply identify the region observed using the endoscope by only taking a look at the image in FIG. 17.

While the processes from S4 to S11 are repeated, the position and the direction of the distal end portion 2d of the insertion portion 2b change. Note that in the 3D model image display section 32, the insertion portion image 32b indicating the sight line direction of the current distal end portion 2d is displayed on the 3D model image 32a, and the inspector can thereby simply understand which part is being currently observed.

When the distal end portion 2d is removed from within the bladder B (S11: YES), the 2D model image display section 31 of the screen G1 displayed on the monitor 6 continues to display the image corresponding when the process is performed on the last acquired endoscope image. The 3D model image display section 32 displays only the 3D model image 32a without displaying the insertion portion image 32b of the insertion portion 2b and the live image display section 33 does not display the live image in the bladder B.

The inspector may record the image of the 2D model image display section 31 in a non-volatile memory section of the memory 22 as data of the clinical record of the patient or print the image and paste it to the clinical record.

Here, transformation between coordinate systems and pasting of an endoscope image will be described.

Figure 18:
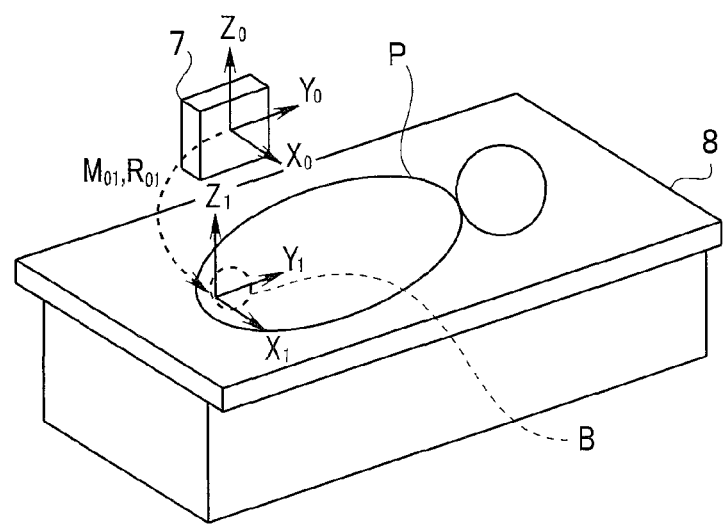
FIG. 18 is a diagram provided for describing a relationship between a coordinate system of a magnetic field generating apparatus 7 and a coordinate system of the bladder B of a patient P on a bed 8 according to the embodiment of the present invention.

FIG. 18 is a diagram provided for describing a relationship between the coordinate system of the magnetic field generating apparatus 7 and the coordinate system of the bladder B of the patient P on the bed 8. The position/direction detection section 25 generates, in real time, position/direction information using the first coordinate system $(X_0 Y_0 Z_0)$ of the magnetic field generating apparatus 7 as a reference.

Then, in S3, the CPU 21 determines the position and the direction of the entrance of the bladder B as a reference position and a reference direction as shown in FIG. 18 and converts the position/direction information of the position/direction detection section 25 to position/direction information in a coordinate system $(X_1 Y_1 Z_1)$ using the entrance of the bladder B as a reference according to the following Equation (3) and Equation (4).

$$P_1 = R_{01} P_0 + M_{01} \qquad \text{Equation (3)}$$

$$V_1 = R_{01} V_0 \qquad \text{Equation (4)}$$

Here, $P_0$ and $V_0$ denote positional and directional vectors respectively in the first coordinate system $(X_0 Y_0 Z_0)$ which is a coordinate system using the magnetic field generating apparatus 7 as a reference. $R_{01}$ is a rotation matrix expressed by the following Equation (5) and $M_{01}$ is a translation matrix expressed by the following Equation (6).

$$R_{01} = \begin{pmatrix} r_{00} & r_{01} & r_{02} \\ r_{10} & r_{11} & r_{12} \\ r_{20} & r_{21} & r_{22} \end{pmatrix} \qquad \text{Equation (5)}$$

$$M_{01} = \begin{pmatrix} m_{x01} \\ m_{y01} \\ m_{z01} \end{pmatrix} \qquad \text{Equation (6)}$$

Thus, a point $(x_0, y_0, z_0)$ in the first coordinate system $(X_0 Y_0 Z_0)$ is converted to a point $(x_1, y_1, z_1)$ in the intermediate coordinate system $(X_1 Y_1 Z_1)$ as shown in the following Equation (7).

$$\begin{pmatrix} x_1 \\ y_1 \\ z_1 \end{pmatrix} = \begin{pmatrix} r_{00} & r_{01} & r_{02} \\ r_{10} & r_{11} & r_{12} \\ r_{20} & r_{21} & r_{22} \end{pmatrix} \begin{pmatrix} x_0 \\ y_0 \\ z_0 \end{pmatrix} + \begin{pmatrix} m_{x01} \\ m_{y01} \\ m_{z01} \end{pmatrix} \qquad \text{Equation (7)}$$

If the positional and directional vectors of the position/direction detection section 25 when the insertion of the distal end portion 2d of the endoscope into the bladder B is detected are assumed to be $P'_0$ and $V'_0$, the translation matrix $M_{01}$ can be obtained according to the following Equation (8).

$$M_{01} = -P'_0 \qquad \text{Equation (8)}$$

Figure 19:
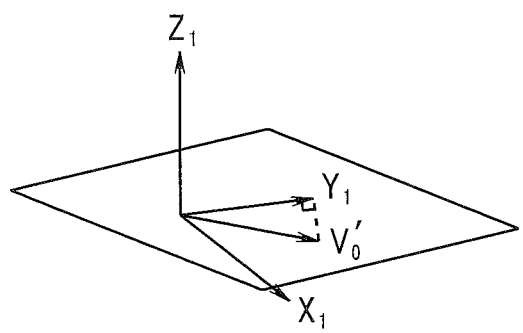
FIG. 19 is a diagram provided for describing directional vectors projected onto an intermediate coordinate system $(X_1Y_1Z_1)$ according to the embodiment of the present invention.

Furthermore, the rotation matrix $R_{01}$ is obtained so as to satisfy the following conditions. FIG. 19 is a diagram provided for describing the directional vector projected onto the intermediate coordinate system $(X_1 Y_1 Z_1)$. The conditions that the rotation matrix $R_{01}$ should satisfy are that $Z_1$ be parallel to the direction of gravity and that $V'_0$ be projected onto the $X_1 Y_1$ plane perpendicular to the $Z_1$, the projected vector direction be $Y_1$, and the vector perpendicular to the $X_1 Y_1$ plane be $X_1$.

Figure 20:
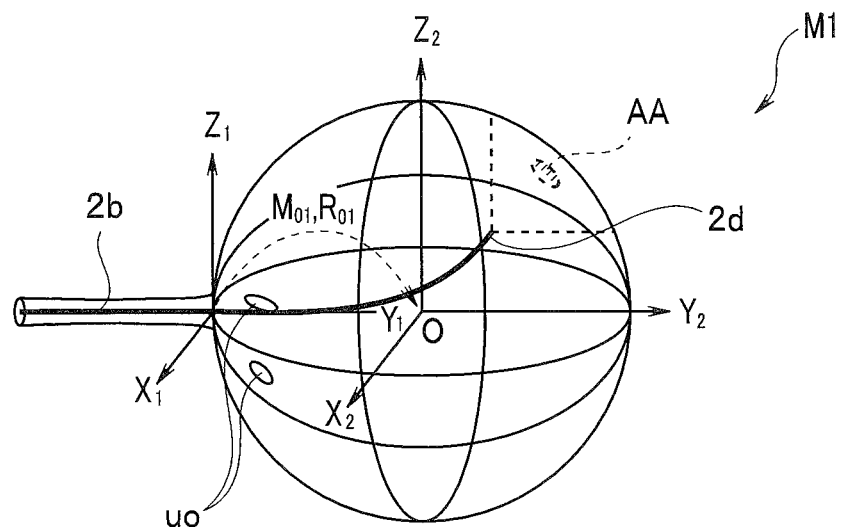
FIG. 20 is a diagram provided for describing a relationship between the intermediate coordinate system $(X_1Y_1Z_1)$ and a second coordinate system $(X_2Y_2Z_2)$ according to the embodiment of the present invention.

Further, in S6, according to the following Equation (9) and Equation (10), the positional and directional vectors of the intermediate coordinate system $(X_1 Y_1 Z_1)$ are converted to positional and directional vectors in the second coordinate system $(X_2 Y_2 Z_2)$ using the center of the 3D bladder model M1 as a reference. FIG. 20 is a diagram provided for describing a relationship between the intermediate coordinate system $(X_1Y_1Z_1)$ and the second coordinate system $(X_2Y_2Z_2)$.

$$P_2 = R_{12}P_1 + M_{02} \quad \text{Equation (9)}$$

$$V_2 = R_{12}V_1 \quad \text{Equation (10)}$$

Here, $P_1$ and $V_1$ are the positional and directional vectors respectively in the intermediate coordinate system $(X_1Y_1Z_1)$ and $P_2$ and $V_2$ are the positional and directional vectors respectively in the second coordinate system $(X_2Y_2Z_2)$. $V_2$ is a directional vector of a pixel at the center of the endoscope image in the second coordinate system $(X_2Y_2Z_2)$. $R_{12}$ is a rotation matrix expressed by the following Equation (11) and $M_{02}$ is a translation matrix expressed by the following Equation (12).

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} \quad \text{Equation (11)}$$

$$M_{02} = \begin{pmatrix} m_{x12} \\ m_{y12} \\ m_{z12} \end{pmatrix} \quad \text{Equation (12)}$$

Thus, the point $(x_1, y_1, z_1)$ in the intermediate coordinate system $(X_1Y_1Z_1)$ is converted to a point $(x_2, y_2, z_2)$ in the second coordinate system $(X_2Y_2Z_2)$ as shown in the following Equation (13).

$$\begin{pmatrix} x_2 \\ y_2 \\ z_2 \end{pmatrix} = \begin{pmatrix} r'_{00} & r'_{01} & r'_{02} \\ r'_{10} & r'_{11} & r'_{12} \\ r'_{20} & r'_{21} & r'_{22} \end{pmatrix} \begin{pmatrix} x_1 \\ y_1 \\ z_1 \end{pmatrix} + \begin{pmatrix} m_{x12} \\ m_{y12} \\ m_{z12} \end{pmatrix} \quad \text{Equation (13)}$$

When the $X_1Y_1Z_1$ coordinate system is moved by $R_2$ in the $Y_1$-axis direction, a translation $M_{12}$ and the rotation $R_{12}$ are as expressed by Equation (14) and Equation (15), respectively.

$$M_{12} = \begin{pmatrix} m_{x12} \\ m_{y12} \\ m_{z12} \end{pmatrix} = \begin{pmatrix} 0 \\ -R_2 \\ 0 \end{pmatrix} \quad \text{Equation (14)}$$

$$R_{12} = \begin{pmatrix} r'_{00} & r'_{01} & r'_{02} \\ r'_{10} & r'_{11} & r'_{12} \\ r'_{20} & r'_{21} & r'_{22} \end{pmatrix} = \begin{pmatrix} 1 & 0 & 0 \\ 0 & 1 & 0 \\ 0 & 0 & 1 \end{pmatrix} \quad \text{Equation (15)}$$

As described above, a position $P_0$ of the first coordinate system $(X_0Y_0Z_0)$ of the magnetic field generating apparatus 7 is converted to a position $P_2$ of the second coordinate system $(X_2Y_2Z_2)$ using the center of the 3D model as a reference according to Equation (7) and Equation (13), and a direction $V_0$ in the first coordinate system $(X_0Y_0Z_0)$ is converted to a direction $V_2$ of the second coordinate system $(X_2Y_2Z_2)$ according to the following Equation (16).

$$V_2 = R_{12}R_{01}V_0 \quad \text{Equation (16)}$$

As for the pasting process of the endoscope image in S7, a calculation of coordinates in the case where an endoscope image is pasted onto the inner surface of the 3D bladder model M1 in the second coordinate system $(X_2Y_2Z_2)$ will be described.

Figure 21:
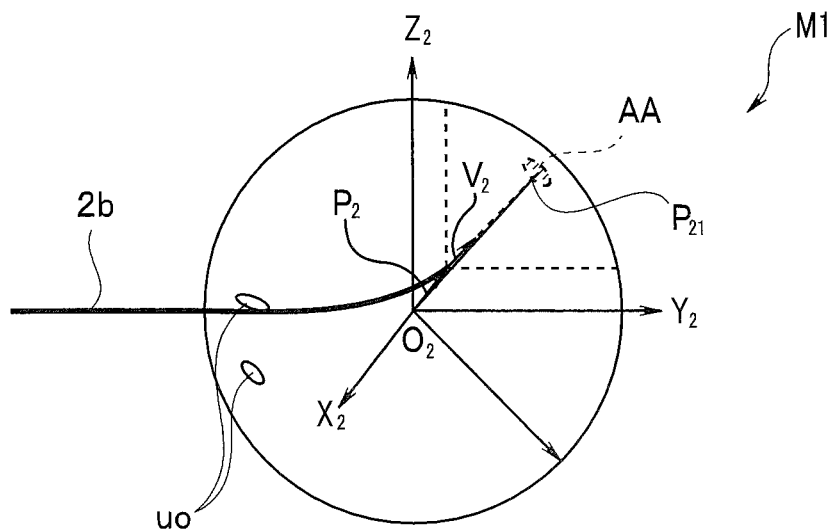
FIG. 21 is a diagram provided for describing coordinates on an inner surface of a sphere in the second coordinate system $(X_2Y_2Z_2)$ according to the embodiment of the present invention.
Figure 22:
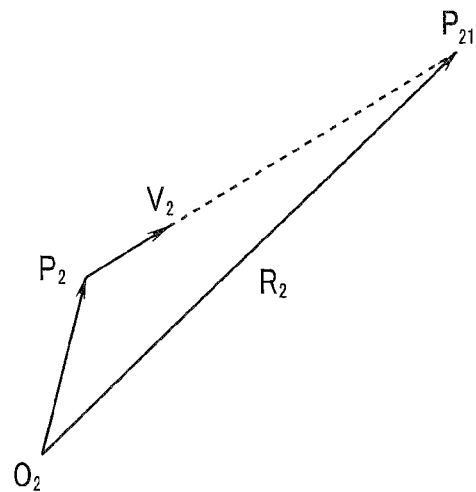
FIG. 22 is a diagram provided for describing a position $P_2$ and a direction $V_2$ in the second coordinate system $(X_2Y_2Z_2)$ from positional and directional vectors of a distal end portion 2d according to the embodiment of the present invention.

The 3D model M1 assumes that the shape of the bladder B is a sphere having a radius R2. The endoscope image is pasted to the inner surface of the sphere. FIG. 21 is a diagram provided for describing coordinates on the inner surface of the sphere in the second coordinate system $(X_2Y_2Z_2)$. FIG. 22 is a diagram provided for describing a position $P_2$ and a direction $V_2$ in the second coordinate system $(X_2Y_2Z_2)$ from the positional and directional vectors of the distal end portion 2d.

After the position $P_2$ and the direction $V_2$ in the second coordinate system $(X_2Y_2Z_2)$ of the distal end portion 2d are determined, coordinates on the inner surface of the sphere of the endoscope image obtained are calculated. For this purpose, a coefficient k that satisfies the following Equation (17) and Equation (18) is calculated and coordinates $P_{21}$ in the second coordinate system $(X_2Y_2Z_2)$ are calculated.

$$P_{21} = P_2 + kV_2 \quad \text{Equation (17)}$$

$$|P_{21}| = R_2 \quad \text{Equation (18)}$$

The endoscope image is projected and pasted at the position of the calculated coordinates $P_{21}$.

Next, the position in the second coordinate system $(X_2Y_2Z_2)$ is projected onto the coordinate system of the 2D model. First, in the case of the hemisphere of the bladder B on the abdomen side ($0 \leq Z_2$), the right and left are inverted on the two-dimensional bladder model, and therefore the value in the u direction is expressed by the following Equation (19) and the value in the v direction is expressed by the following Equation (20).

$$u = -x_{21} \quad \text{Equation (19)}$$

$$v = y_{21} + R_2 \quad \text{Equation (20)}$$

In the case of the hemisphere of the bladder B on the back side ($Z_2 < 0$), the right and left are inverted on the two-dimensional bladder model, and therefore the value in the u direction is expressed by the following Equation (21) and the value in the v direction is expressed by the following Equation (22).

$$u = x_{21} \quad \text{Equation (21)}$$

$$v = -y_{21} - R_2 \quad \text{Equation (22)}$$

Figure 23:
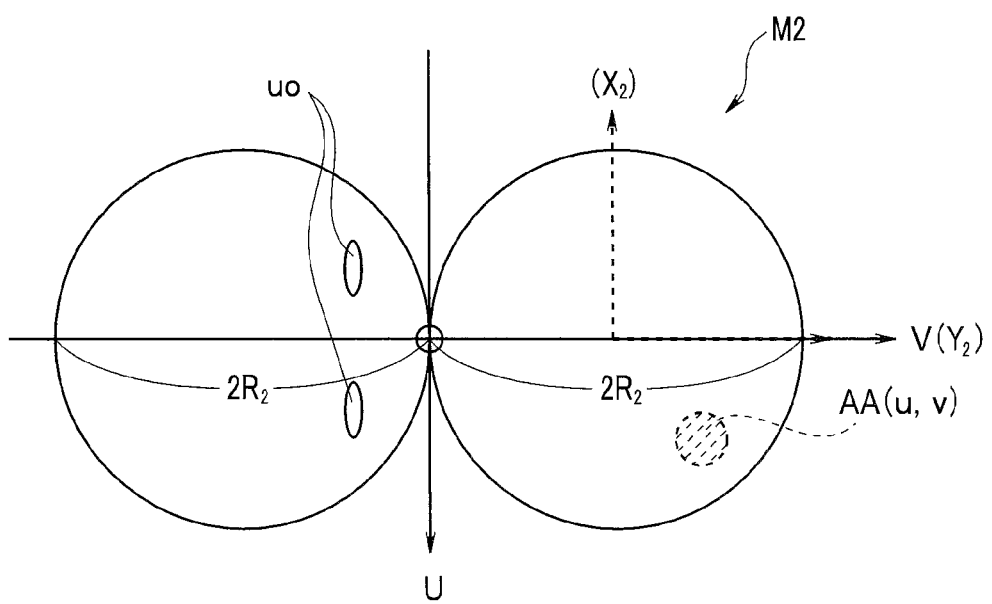
FIG. 23 is a diagram provided for describing a coordinate relationship in a two-dimensional coordinate system (U,V) according to the embodiment of the present invention.

FIG. 23 is a diagram provided for describing a coordinate relationship in the two-dimensional coordinate system (U,V).

The directional vector $V_2$ is a directional vector of a pixel at the center of the endoscope image in the second coordinate system $(X_2Y_2Z_2)$ as described above. Therefore, it is possible to paste the whole endoscope image to the inner surface of the sphere of the second coordinate system $(X_2Y_2Z_2)$ by calculating a directional vector of each pixel for pixels other than the pixels at the center of the image of the endoscope image and repeating the conversion calculations of the aforementioned Equation (17) to Equation (22).

Figure 24:
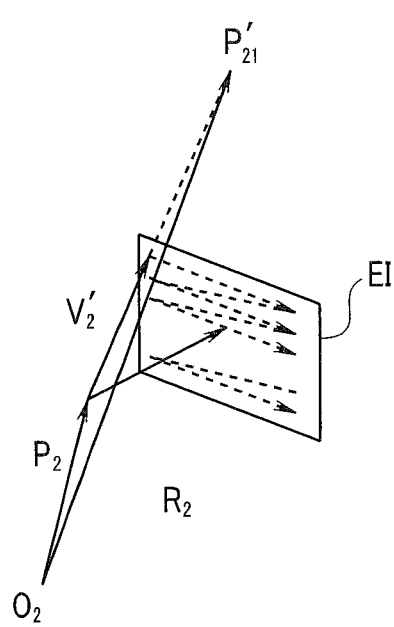
FIG. 24 is a diagram provided for describing operation of scanning a whole endoscope image and pasting each pixel onto the inner surface of the sphere of the second coordinate system $(X_2Y_2Z_2)$ according to the embodiment of the present invention.

FIG. 24 is a diagram provided for describing scanning the whole endoscope image and pasting of each pixel onto the inner surface of the sphere of the second coordinate system $(X_2Y_2Z_2)$. Each pixel is pasted onto the inner surface of the sphere of the second coordinate system $(X_2Y_2Z_2)$ while each pixel of an endoscope image EI is scanned in a predetermined direction as shown by a dotted line. In FIG. 24, $V_2'$ denotes a pasting vector of each pixel of the endoscope image EI and $P_{21}'$ denotes a pasting vector of the inner surface of the sphere of the second coordinate system $(X_2Y_2Z_2)$.

As described above, according to the present embodiment, since the endoscope image of the inspected part of the interior of the bladder B is superimposed on the 2D model image 31a and the endoscope image when the release button 13 is pressed is superimposed and displayed so that it comes to the forefront on the 2D model image 31a, the inspector can simply confirm the region checked in the bladder B and clearly observe the image of the lesioned part or a region that the inspector is concerned about.

Note that when pasting the endoscope image onto the 2D model image 31a, only the endoscope image when the release button 13 is pressed may be pasted.

Figure 25:
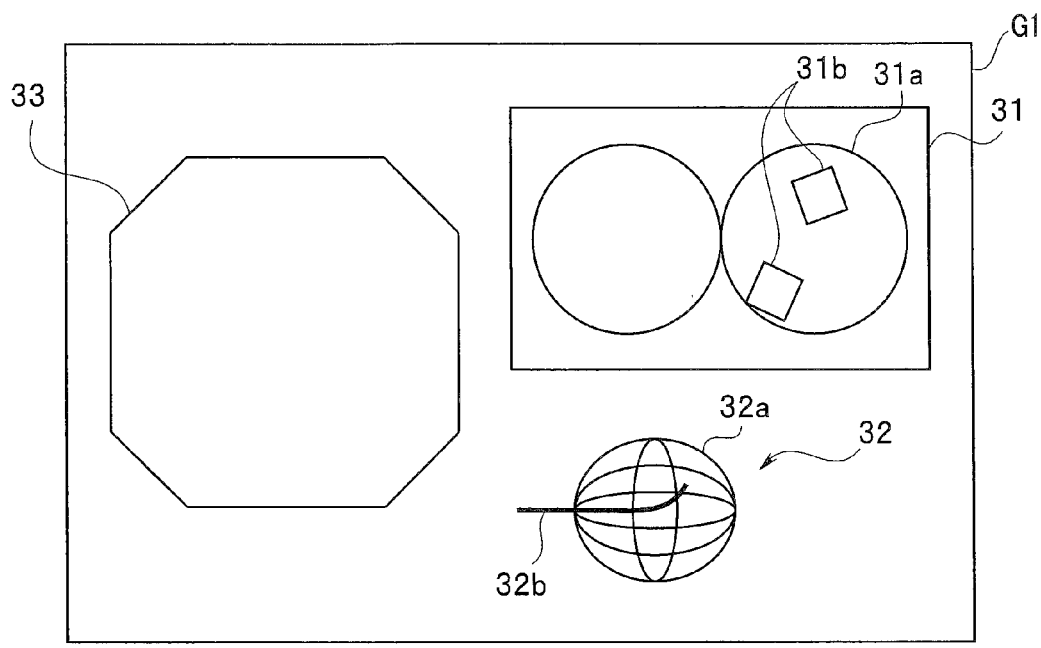
FIG. 25 is a diagram illustrating another example of an image displayed on the screen of the monitor 6 according to the embodiment of the present invention.

FIG. 25 is a diagram illustrating another example of the image displayed on the screen of the monitor 6. In the 2D model image display section 31, only the endoscope image when the release button 13 is pressed is pasted onto the 2D model image 31a. The inspector may record also the image of the 2D model image display section 31 in FIG. 25 in a non-volatile memory portion of the memory 22 as data of the clinical record of the patient or may print the image and paste it to the clinical record.

Since the magnetic sensor 12 in the aforementioned example is a 6-axis sensor, a plurality of endoscope images are pasted onto the 2D model image so that the vertical and horizontal directions of those images match each other. However, the magnetic sensor 12 may also be a 5-axis sensor.

Figure 26:
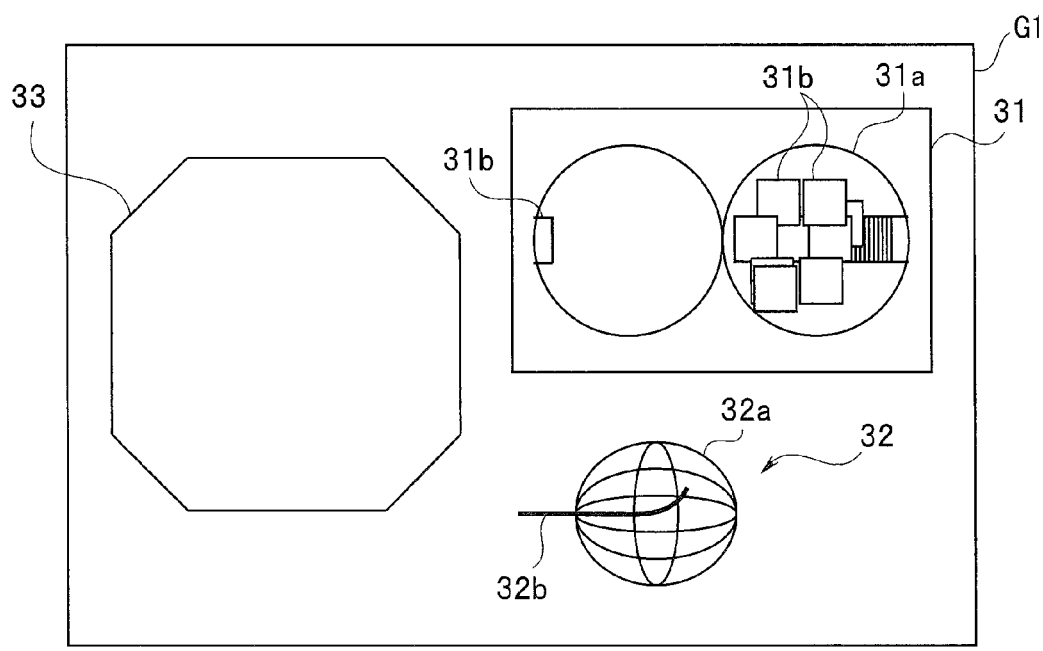
FIG. 26 is a diagram illustrating an example of an image displayed on the screen of the monitor 6 when a 5-axis sensor is used according to the embodiment of the present invention.
Figure 27:
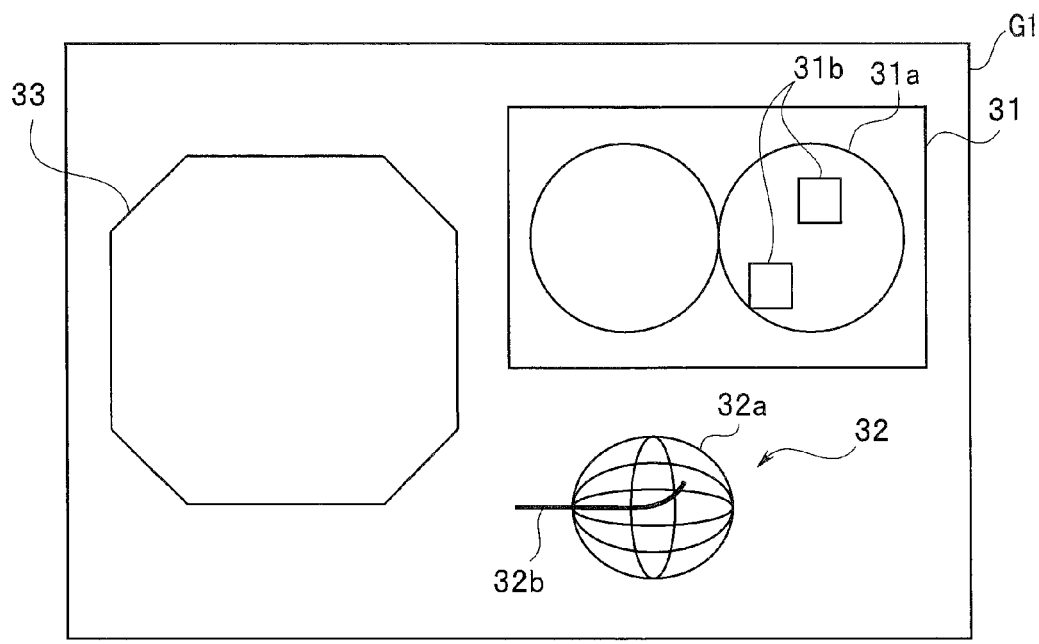
FIG. 27 is a diagram illustrating an image example in which only an endoscope image is pasted onto the 2D model image 31a when a release button 13 is pressed in the case where the 5-axis sensor is used according to the embodiment of the present invention.

FIG. 26 is a diagram illustrating an example of an image displayed on the screen of the monitor 6 when a 5-axis sensor is used. FIG. 27 is a diagram illustrating an example of an image in which only the endoscope image when the release button 13 is pressed is pasted onto the 2D model image 31a when the 5-axis sensor is used. FIG. 26 corresponds to FIG. 17 and FIG. 27 corresponds to FIG. 25.

When the magnetic sensor 12 is a 5-axis sensor, it is not possible to detect the rotation angle around the axis of the insertion portion 2b, but as shown in FIG. 26 and FIG. 27, each endoscope image 31b is pasted onto the 2D model image 31a at a predetermined angle irrelevant to the rotation around the axis of the insertion portion 2b.

Effects similar to those in the aforementioned embodiment can be achieved also using the 5-axis sensor.

Furthermore, in the aforementioned example, an endoscope image in a normal-light observation mode is pasted onto the organ model image, but an endoscope image in a special-light observation mode may also be pasted onto the organ model image.

In this case, the endoscope image 31b in the aforementioned FIG. 17 and FIG. 25 to FIG. 27 is not an endoscope image with normal light but an endoscope image with special light (narrow-band light here).

Two organ model images may be displayed; an endoscope image with normal light may be pasted to one of the model images and an endoscope image with special light may be pasted to the other.

Figure 28:
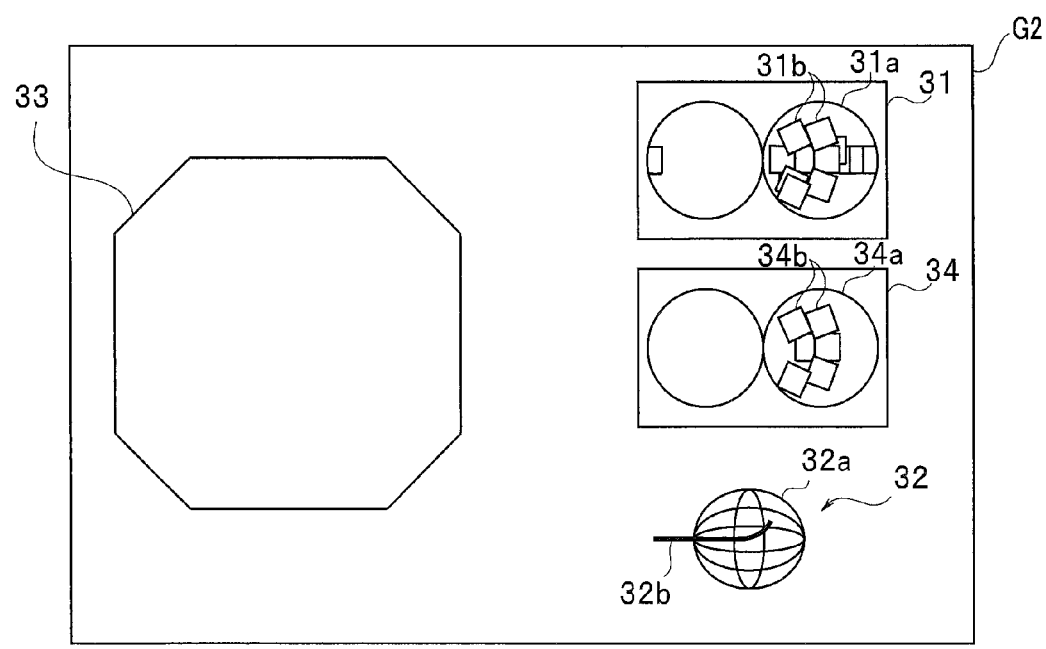
FIG. 28 is a diagram illustrating a display screen example when two organ model images are displayed in correspondence with two observation modes according to the embodiment of the present invention.

FIG. 28 is a diagram illustrating an example of a display screen when two organ model images corresponding to the two observation modes are displayed.

In FIG. 28, the same components as those in FIG. 17 and FIG. 25 to FIG. 27 are assigned the same reference numerals and characters and description thereof is omitted. Note that FIG. 28 illustrates an example using a 6-axis sensor.

In FIG. 28, in addition to the organ model image of the endoscope image with normal light, a 2D model image display section 34 for pasting an endoscope image with special light is added on the screen.

The 2D model image display section 34 displays a 2D model image 34a and an endoscope image 34b with special light pasted onto the 2D model image 34a through the processes in S7 and S9.

Since the 2D model image display section 31 displays the endoscope image with normal light and the 2D model image display section 34 displays the endoscope image with narrow-band light, the inspector can perform an inspection or the like while comparing both, and also in subsequent inspections, the inspector can know the state of the organ in previous inspections in further detail if both images are attached to the clinical record.

Thus, in S7 constituting the image generation section, a plurality of model images are set and endoscope images corresponding to the type of illuminating light are pasted onto the plurality of models set based on the type of illuminating light of the light source apparatus 4, which is the illumination section.

Note that since the endoscope image with narrow-band light shows more detailed texture of the interior of the mucous membrane surface than the endoscope image with normal light, it may also be possible to paste the endoscope image with narrow-band light when the release button is pressed onto the 2D model image 31a of the 2D model image display section 31 such that the endoscope image with narrow-band light is pasted onto the forefront, and generate an image in which both the endoscope image with normal light and the endoscope image with narrow-band light are pasted onto one 2D model image display section.

Note that since the inspector observing the endoscope image can know that the distal end portion 2d enters the bladder from a change in the endoscope image displayed on the monitor 6, when the distal end portion 2d enters the bladder B, the inspector may perform a predetermined operation on the operation portion 2a or the operation panel of the processor 5 and thereby record a reference position and direction. That is, the position and the direction of the objective optical window 11a may be aligned with the coordinate system of the organ model image based on the predetermined operation input by the inspector.

The inspector specifies a position at which the distal end portion 2d enters the bladder through the urethra outside the body cavity and sets a plane in which the position is included (plane perpendicular to the $Y_1$ direction of the coordinate system $(X_1Y_1Z_1)$ using the entrance of the bladder B as a reference). When the endoscope is inserted into the urethra, and the position and the direction thereof when the endoscope passes through the plane may be recorded as a reference position and direction. That is, the position and the direction of the objective optical window 11a may be aligned with the coordinate system of the organ model image based on the position information with respect to the preset reference plane.

As described above, according to the aforementioned endoscope system of the present embodiment, it is possible to implement an endoscope system and an endoscope image processing method whereby an inspector can easily grasp a position of an endoscope image in an organ to be inspected and a clear endoscope image can be pasted onto an organ model image of the target organ.

According to the aforementioned endoscope system of the present embodiment, it is possible to easily confirm a position of a lesioned part in the bladder B and a region being observed, and thereby prevent overlook of the lesioned part, reduce a re-inspection rate or reduce writing errors in a clinical record.

Note that in the aforementioned embodiment, endoscope images captured by the image pickup device 11 are stored temporarily in the memory 22, and when the recorded endoscope images are pasted onto a model image, only clear images are selected, but when endoscope images captured by the image pickup device 11 are stored in the memory 22, only clear images may be selected.

That is, a determination in S22 is made before the recording process in S7, and in the recording process in S7, a subject internal image determined to be an image that can be pasted and position information acquired by the position information acquiring section are stored in association with each other in the memory 22, and then an image pasting process in S24 is executed.

For example, the determining process executed in S22 through the processes in FIG. 10 to FIG. 13 is executed through the recording process (S7) in which the endoscope image obtained from the image pickup device 11 is stored. In this case, the process in S22 executed in the recording process constitutes a determining section that determines whether or not to perform recording in the recording process based on the image information or the position information of the subject internal image acquired by the image pickup device 11.

In this way, even when the process of selecting only a clear image is executed in the recording process, it is possible to obtain effects similar to those in the aforementioned embodiment, and further, since the number of endoscope images stored in the memory 22 is reduced, there is also an effect that only a small storage capacity of the memory 22 is required.

Note that in addition, some of various processes of selecting clear endoscope images may be executed in the recording process in S7 and the remaining processes may be executed in the image pasting process. For example, the determining process through image processing may be executed in the recording process in S7, and the determining process according to position/direction information, and the determining process according to the distance to the bladder wall surface and the sight line direction may be executed in the image pasting process in S8.

Note that in addition, in the aforementioned embodiment, the endoscope image is pasted onto the two-dimensional organ model image, but the endoscope image may also be pasted onto a three-dimensional organ model image which is a 3D image. That is, the model image may be a 3D image instead of a 2D image.

Furthermore, in the aforementioned embodiment, the endoscope image of the interior of the bladder is pasted onto a 2D model image of the bladder, but the aforementioned endoscope system of the embodiment is also applicable to organs other than the bladder, such as the stomach and uterus.

In the case of the stomach, when the endoscope enters the stomach from the esophagus, or in the case of the lung, when the trachea first branches, in the lower part thereof, into the left and right tracheas or in the case of the uterus, when the endoscope enters the uterus from the cervix of uterus, it is possible to determine reference information from a change in images and paste the images onto the organ model image.

In the aforementioned embodiment, the endoscope 2 is a flexible endoscope having a flexible insertion portion, but the present invention is also applicable to endoscopes of other types such as a rigid endoscope or scanning-type endoscope, and further applicable to an endoscope whose insertion portion includes a light guide member that guides light incident on an objective optical window at a distal end portion to a proximal end portion.

Moreover, while the aforementioned endoscope system is used to record or display the position of the endoscope image inside an organ, the endoscope system can also be used to record a biopsy position in random biopsy.

The present invention is not limited to the aforementioned embodiment, but various modifications or alterations or the like can be made thereto without departing from the spirit and scope of the present invention.

What is claimed is:

1. An endoscope system comprising:
    an insertion portion that is inserted into a subject;
    an objective optical window provided on a distal end side of the insertion portion to receive light from the subject;
    an image sensor that picks up an image of an interior of the subject using the light incident on the objective optical window;
    a memory that stores a predetermined organ model image of the subject; and
    a controller configured to:
        acquire position/direction information of the objective optical window;
        record, in the memory, a subject internal image acquired by the image sensor and the acquired position/direction information in association with each other;
        determine whether or not the image sensor is moving at a predetermined speed or higher based on the position/direction information and determine, when the image sensor is not moving at the predetermined speed or higher, that the subject internal image is an image that can be pasted onto a model image of the predetermined organ in a state where the position/direction information of the objective optical window and the position/direction information in a coordinate system of the predetermined organ model image are associated with each other; and
        read the subject internal image determined to be the image that can be pasted from the memory and paste the subject internal image onto the model image of the predetermined organ based on the position/direction information.

2. The endoscope system according to claim 1, further comprising a light source that radiates white light or narrow-band light having a predetermined wavelength band onto the subject in a manner switchable therebetween,
    wherein the controller is further configured to set a plurality of model images of the predetermined organ and paste the subject internal image onto the model image based on the type of illuminating light.

3. The endoscope system according to claim 1,
    wherein the subject internal image is an image of an interior of a bladder of the subject, and
    the model image is a model image of the bladder.

4. The endoscope system according to claim 3, wherein the model image is a 2D developed view of the bladder.

5. The endoscope system according to claim 1, wherein the model image is a 3D image or a 2D image.

* * * * *